US011859223B2

(12) United States Patent
Avalos et al.

(10) Patent No.: US 11,859,223 B2
(45) Date of Patent: Jan. 2, 2024

(54) SYSTEM AND METHOD OF OPTOGENETICALLY CONTROLLING METABOLIC PATHWAYS FOR THE PRODUCTION OF CHEMICALS

(71) Applicant: The Trustees of Princeton University, Princeton, NJ (US)

(72) Inventors: Jose L. Avalos, Princeton, NJ (US); Jared E. Toettcher, Princeton, NJ (US); Evan M. Zhao, Clarence Center, NY (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 0 days.

(21) Appl. No.: 16/091,624

(22) PCT Filed: Apr. 7, 2017

(86) PCT No.: PCT/US2017/026615
§ 371 (c)(1),
(2) Date: Oct. 5, 2018

(87) PCT Pub. No.: WO2017/177147
PCT Pub. Date: Oct. 12, 2017

(65) Prior Publication Data
US 2019/0119331 A1    Apr. 25, 2019

Related U.S. Application Data

(60) Provisional application No. 62/468,071, filed on Mar. 7, 2017, provisional application No. 62/319,704, filed on Apr. 7, 2016.

(51) Int. Cl.
*C12P 7/56* (2006.01)
*C12N 9/04* (2006.01)
(Continued)

(52) U.S. Cl.
CPC ............ *C12N 9/88* (2013.01); *C12N 9/0006* (2013.01); *C12N 9/1022* (2013.01); *C12N 13/00* (2013.01);
(Continued)

(58) Field of Classification Search
CPC ...... C12N 9/0006; C12N 9/1022; C12N 9/88; C12P 7/56
See application file for complete search history.

(56) References Cited

U.S. PATENT DOCUMENTS 5,416,008 A    5/1995  Bailey
9,506,073 B2 *  11/2016  Gardner ............... C12N 9/0069
(Continued)

FOREIGN PATENT DOCUMENTS

WO    WO-2015020649 A1 *  2/2015  ............ C12N 15/81
WO    2015191638 A1    12/2015

OTHER PUBLICATIONS

Tokuhiro. Double mutation of the PDC1 and ADH1 genes improves lactate production in the yeast *Saccharomyces cerevisiae* expressing the bovine lactate dehydrogenase gene Appl Microbiol Biotechnol (2009) 82:883-890.*
(Continued)

*Primary Examiner* — Yong D Pak
(74) *Attorney, Agent, or Firm* — MEAGHER EMANUEL LAKS GOLDBERG & LIAO, LLP

(57) ABSTRACT

A system and method for controlling metabolic enzymes or pathways in cells to produce a chemical above the levels of a wild-type strain is disclosed. The system utilizes cells, including yeasts, bacteria, and molds, having at least two genes capable of being controlled bi-directionally with light, where one gene is turned from off to on when exposed to light and another gene is turned from on to off when exposed to light, the two genes reversing when the light is turned off.

(Continued)

Cells may utilize any number of sequences that benefit chemical production, including sequences that: encode for constitutive transcription of light-activated transcription factor fusions; encode for a metabolic enzyme; encode for a repressor; induce expression of metabolic enzymes; and an endogenous or exogenous activator expressed by a constitutive promoter, inducible promoter, or gene circuit. These systems may be coupled to biosensors or protein cascade systems, enabling the monitoring or automation of the fermentation process to optimize production of a desired product. These systems may also allow for optimization and periodic operation of a bioreactor using light pulses.

4 Claims, 28 Drawing Sheets

Specification includes a Sequence Listing.

(51) Int. Cl.
    *C12N 9/88* (2006.01)
    *C12N 9/10* (2006.01)
    *C12N 13/00* (2006.01)
    *C12P 7/16* (2006.01)
    *C12N 15/81* (2006.01)
    *C12N 15/63* (2006.01)

(52) U.S. Cl.
    CPC ........... *C12N 15/63* (2013.01); *C12N 15/635* (2013.01); *C12N 15/81* (2013.01); *C12P 7/16* (2013.01); *C12P 7/56* (2013.01); *C12Y 101/01027* (2013.01); *C12Y 202/01006* (2013.01); *C12Y 401/01001* (2013.01)

(56) References Cited

U.S. PATENT DOCUMENTS

| | | | |
|---|---|---|---|
| 2003/0082809 | A1 | 5/2003 | Quail et al. |
| 2004/0038400 | A1 | 2/2004 | Froehlich et al. |
| 2013/0130341 | A1 | 5/2013 | Liao et al. |
| 2013/0345294 | A1 | 12/2013 | Yang et al. |
| 2014/0011264 | A1 | 1/2014 | Duhring et al. |
| 2014/0325692 | A1* | 10/2014 | Gardner ............... C12N 9/0069 800/13 |

OTHER PUBLICATIONS

International Search Report for PCT/US2017/026615, dated Jul. 6, 2017.
Written Opinion for PCT/US2017/026615, dated Jul. 6, 2017.
Renicke et at."A LOV2 Domain-Based Optogenetic Tool to Control Protein Degradation and Cellular Function," Chemistry & Biology, Apr. 18, 2013 (Ape. 18, 2013}, vol. 20. pp. 619-626.
Hughes et al. "Light-Mediated Control of DNA Transcription in Yeast," Methods, Dec. 31, 2012 (Dec. 31, 2012), vol. 58, pp. 385-391.
Salinas et al. "Optogenetic Switches for Light-Controlled Gene Expression In Yeast." Applied Microbiology and Biotechnology, Apr. 2, 2017 (Apr. 1, 2017).vol. 101, pp. 2629-2640.
Ajikumar et al. "Isoprenoid Pathway Optimization for Taxol Precursor Overproduction in *Escherichia coli*", Science. Oct. 1, 2010; 330(6000): 70-74. doi:10.1126/science.1191652.
Brinkmann-Chen et al. "General approach to reversing ketol-acid reductoisomerase cofactor dependence from NADPH to NADH", PNAS, vol. 110, No. 27, pp. 10946-10951, Jul. 2, 2013.
Gueldener et al. "A second set of loxP marker cassettes for Cre-mediated multiple gene knockouts in budding yeast", Nucleic Acids Research, vol. 30, No. 6 e23, 2002.
Jayaraman et al. "Blue light-mediated transcriptional activation and repression of gene expression in bacteria", Nucleic Acids Research, 2016, doi: 10.1093/nar/gkw548.
Kennedy et al. "Rapid blue light induction of protein interactions in living cells", Nat Methods. Dec. 2010 ; 7(12): 973-975. doi:10.1038/nmeth.1524.
Milias-Argeitis et al. "Automated optogenetic feedback control for precise and robust regulation of gene expression and cell growth", Nature communications, DOI: 10.1038/ncomms12546, Aug. 26, 2016.
Matsuda et al. "Increased isobutanol production in *Saccharomyces cerevisiae* by eliminating competing pathways and resolving cofactor imbalance", Microbial Cell Factories 2013, 12:119.
Motta-Mena et al. "An optogenetic gene expression system with rapid activation and deactivation kinetics", Nat Chem Biol. Mar. 2014 ; 10(3): 196-202. doi:10.1038/nchembio.1430.
Müller et al. "Multi-chromatic control of mammalian gene expression and signaling", Nucleic Acids Research, 2013, vol. 41, No. 12 e124, doi:10.1093/nar/gkt340.
Nash et al. "Structural basis of photosensitivity in a bacterial light-oxygen-voltage/helix-turn-helix (LOV-HTH) DNA-binding protein", PNAS, vol. 108, No. 23, pp. 9449-9454, Jun. 7, 2011.
Ottoz et al. "Inducible, tightly regulated and growth condition-independent transcription factor in *Saccharomyces cerevisiae*", Nucleic Acids Research, 2014, vol. 42, No. 17 e130, doi: 10.1093/nar/gku616.
Pathak et al. "Benchmarking of Optical Dimerizer Systems", ACS Synth. Biol. 2014, 3, 832-838, dx.doi.org/10.1021/sb500291r.
Rivera-Cancel et al. "Identification of natural and artificial DNA substrates for the light-activated LOV-HTH transcription factor EL222", Biochemistry. Dec. 18, 2012; 51(50): 10024-10034. doi:10.1021/bi301306t.
Ro et al. "Production of the antimalarial drug precursor artemisinic acid in engineered yeast", Nature, vol. 440, Apr. 13, 2006.
Shimizu-Sato et al. "A light-switchable gene promoter system", Nature Biotechnology, vol. 20, Oct. 2002.
Da Silva et al. "Introduction and expression of genes for metabolic engineering applications in *Saccharomyces cerevisiae*", FEMS Yeast Res. Mar. 2012;12(2):197-214. doi: 10.1111/j.1567-1364.2011.00769. x. Epub Jan. 12, 2012.
Usherenko et al. "Photo-sensitive degron variants for tuning protein stability by light", BMC Systems Biology 2014, 8:128.
Zoltowski et al. "Blue-light induced dimerization of a bacterial LOV-HTH DNA-binding protein", Biochemistry. Sep. 24, 2013; 52(38): . doi:10.1021/bi401040m.

\* cited by examiner

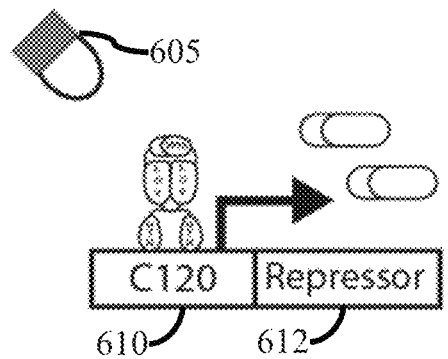
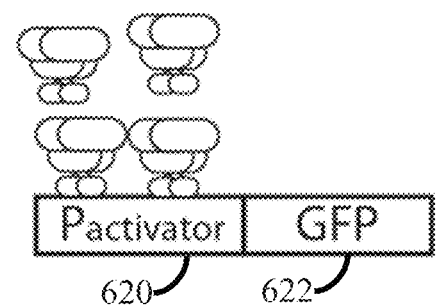
FIG. 7A            FIG. 7B
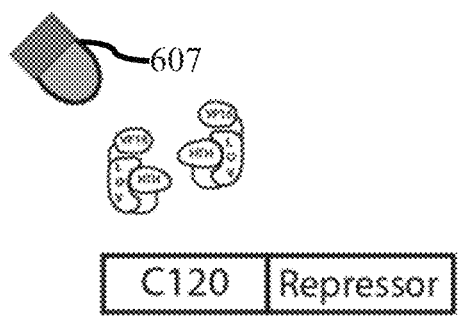
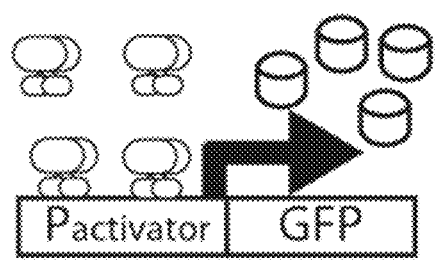
FIG. 7C            FIG. 7D

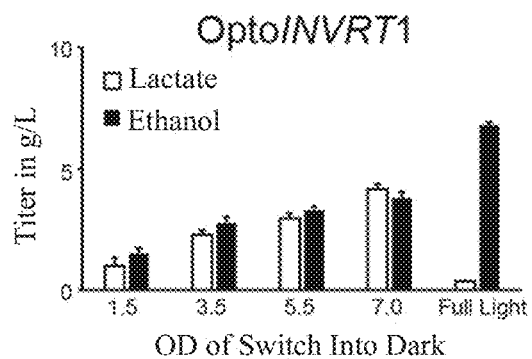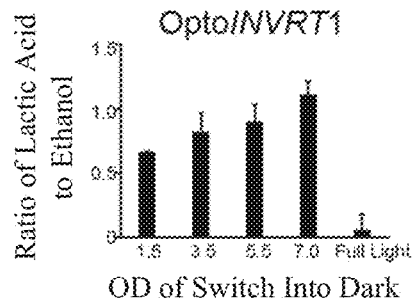
FIG. 13A  FIG. 13B
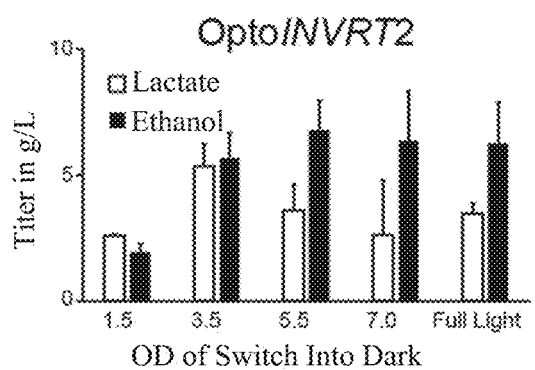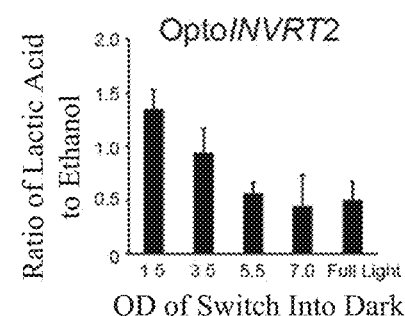
FIG. 13C  FIG. 13D
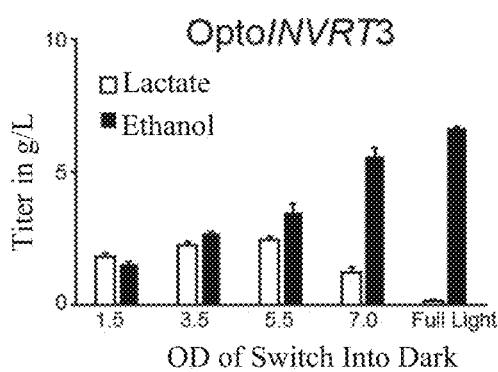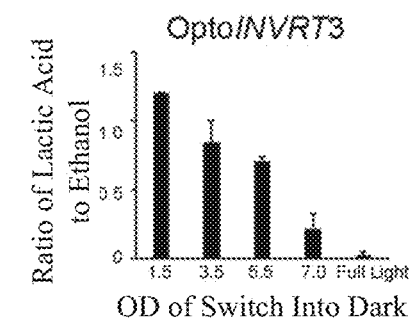
FIG. 13E  FIG. 13F

SYSTEM AND METHOD OF OPTOGENETICALLY CONTROLLING METABOLIC PATHWAYS FOR THE PRODUCTION OF CHEMICALS

CROSS-REFERENCE TO RELATED APPLICATIONS

This application claims benefit of U.S. Patent Application Nos. 62/319,704, filed Apr. 7, 2016, and 62/468,071, filed Mar. 7, 2017, both of which are hereby incorporated in its entirety by reference.

BACKGROUND

Metabolic engineering aims to rewire the metabolism of organisms ranging from bacteria to mammalian cells for efficient conversion of inexpensive substrates into valuable products, such as chemicals, fuels, or drugs. This involves genetically modifying the host organism to express enzymes for the biosynthetic pathway of interest and deleting endogenous genes that compete for resources with this pathway. Fine-tuning the timing and expression levels of enzymes involved in a biosynthetic pathway can relieve bottlenecks and minimize its metabolic burden. This is critical when the product of interest or its precursors are toxic, or when the biosynthetic pathway of interest competes with endogenous pathways that are essential for cell growth.

To address these challenges, metabolic engineers frequently use inducible systems to control gene expression of engineered metabolic pathways, and separate cell growth from product formation. Inducible systems currently used in metabolic engineering are controlled by chemical inducers or repressors. Some promoters in Saccharomyces cerevisiae are regulated by the carbon source, such as $P_{GAL1}$, $P_{GAL10}$ and $P_{ADH2}$, which are repressed by glucose and induced by galactose and ethanol, respectively. There are also promoters regulated by nutrients, for example $P_{MET3}$, which is repressed when methionine is present in the medium, and induced when it is absent. Other promoters are induced by specific ligands such as copper, tetracycline/doxycycline, or β-estradiol. Although some of these systems allow for tight regulation of gene expression, the use of chemicals necessarily place restrictions on media composition. Moreover, chemical inducers and repressors are relatively coarse and persistent, making their effects difficult to tune and practically impossible to reverse.

Light is an attractive substitute for chemicals to address the deficiencies in existing inducible systems. Light is non-toxic and inexpensive compared to chemical inducers, and is compatible with any carbon source or nutrient composition. Furthermore, unlike chemicals, light can be delivered or removed instantaneously with precise control over light intensity or exposure periods. This could greatly simplify and improve the optimization of expression levels of enzymes in engineered metabolic pathways, providing new time-varying modes of control that are not possible with chemical inducers. In recent years, light-switchable transcription modules have been shown to enable tunable gene expression in a variety of organisms, including yeast. However, to date, it has not been possible for optogenetics to be used as a complete solution for metabolic engineering applications, to control rewired cellular metabolisms for the production of valuable products.

BRIEF DESCRIPTION OF THE DRAWINGS

FIGS. 7A, 7B, 7C, and 7D illustrate a method of activation and repression of a gene utilizing an embodiment of an OptoINVRT circuit.

FIGS. 13A, 13C, and 13E are graphs of OptoINVRT1, OptoINVRT2, and OptoINVRT3 (respectively) embodiment titers of Lactate and Ethanol moved into darkness at different ODs.

FIGS. 13B, 13D, and 13F are graphs of the ratios of lactic acid to ethanol production for OptoINVRT1, OptoINVRT2, and OptoINVRT3 (respectively) embodiments moved into darkness at different ODs.

DETAILED DESCRIPTION

Figure 1:
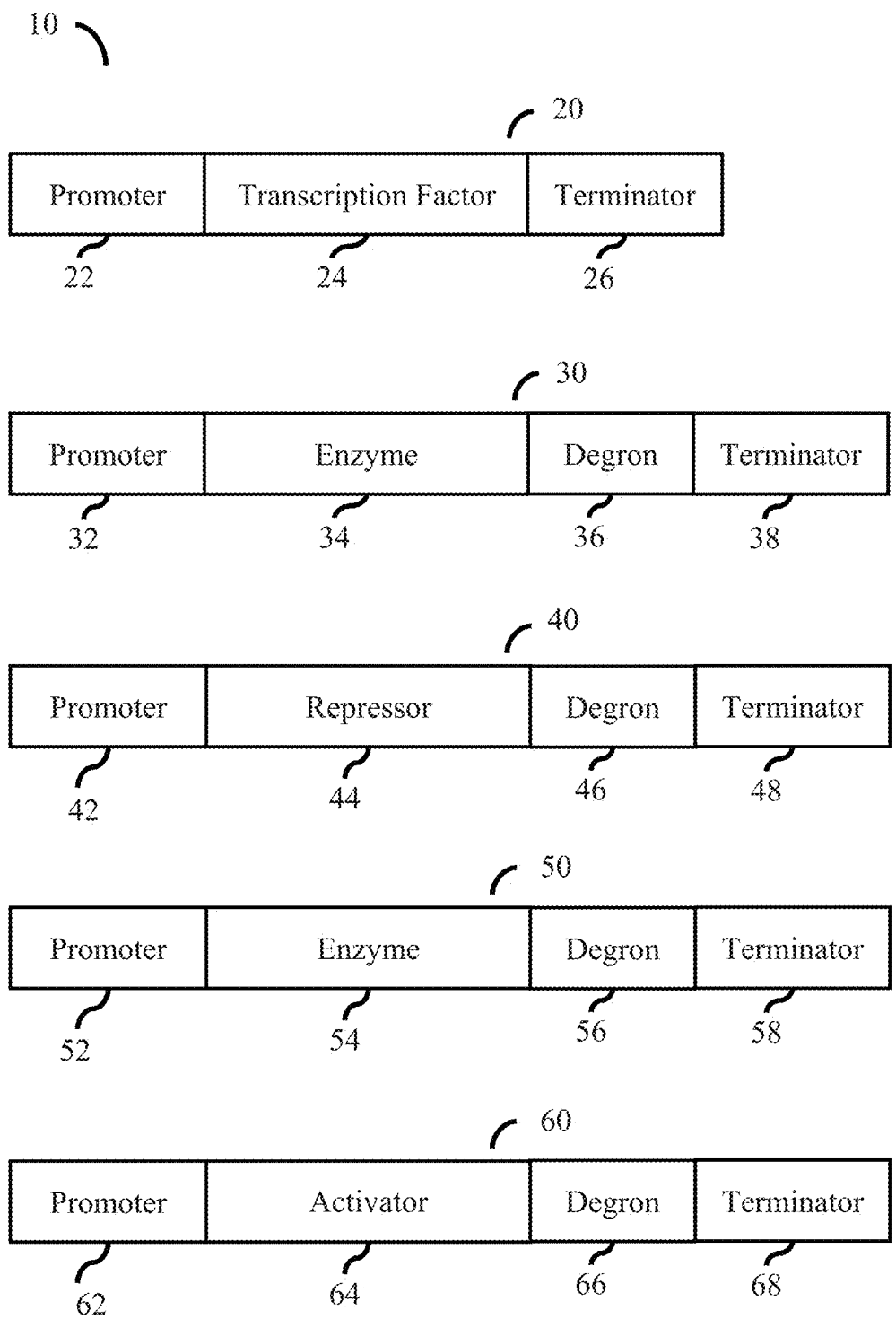
FIG. 1 is a diagram depicting five general components of the present invention.

Here, the disclosure is drawn to a method and system for using light to control the expression of genes involved in the biosynthesis of desirable, valuable products.

Specifically, disclosed is a combination of two novel systems for light-controlled gene expression in yeast, Opto-EXP and OptoINVRT, based on the EL222 light-sensitive transcription factor from *Erythrobacter litoralis* (Nash PNAS 2011). Using these two systems, it is possible to strongly activate and repress distinct sets of genes in a light-dependent manner. This bidirectional control makes it possible to tune the expression of endogenous metabolic pathways essential for growth, as well as engineered biosynthetic pathways for products of interest, to achieve a shift between growth and production phases using light. In some embodiments, this approach is shown as being applicable for production of two valuable products, designing yeast strains that grow robustly on glucose by maintaining wild-type ethanol production under light and then produce lactate or isobutanol (as well as 2-methyl-1-butanol) upon shifting the cells to darkness. In addition, by varying the schedule of illumination during the production phase of fermentation, it is possible to achieve high yields of desired chemical production, such as isobutanol production.

The disclosed system and method can be applied across a variety of organisms, including but not limited to yeasts, bacteria, and molds.

A preferred embodiment of the present invention utilizes a yeast cell comprising a plurality of genes capable of being controlled bi-directionally with at least one wavelength of light. Thus, in general, the yeast cell should comprise two or more genes capable of being controlled bi-directionally with light, where one gene is turned from off to on when exposed to light (and then turned from on to off when not exposed to that light or when exposed to a different wavelength of light), and another gene that turned from on to off when exposed to light (and then turned from off to on when not exposed to that light or when exposed to a different wavelength of light). In preferred embodiments, the first gene and second gene are metabolic enzymes, and in more preferred embodiments, the metabolic enzymes compete for at least one resource, which includes but is not limited to metabolites, proteins, or nutrients. In certain embodiments, the metabolic enzymes are selected so as to allow or enable the cell to overproduce a desired chemical, by producing an amount of that chemical that is greater than what is produced by a wild-type strain. In some embodiments, that overproduced chemical is toxic to the yeast cell, such as lactic acid, isobutanol, isopentanol (3-methyl-1-butanol), or 2-methyl-1-butanol. In some embodiments, one or more of the enzymes are essential for cell growth. The preferred yeast cell is derived from *Saccharomyces Cerevisiae*, although other species of yeast are also envisioned. In still more preferred embodiments, the yeast cell is constructed such that the first gene comprises GAL80 or PDC1, and/or the second gene comprises ILV2 or LDH.

Referring to FIG. 1, a generalized system (10) of one embodiment of the present invention is disclosed. In the system (10), five protein constructs or sequences (20, 30, 40, 50, 60) are provided.

The first sequence (20) comprises a promoter (22), and a gene encoding a light-activated transcription factor (which may be comprised of a fusion of a plurality of protein sequences), such that binding to promoter sequences and gene transcription are initiated under certain wavelengths (24). The first sequence (20) may also comprise a terminator (26). Preferred embodiments of the promoter (22) utilize promoters that are expressed during growth on a particular substrate, such as glucose. More preferred embodiments utilize the constitutive promoter for TEF1 ($P_{TEF1}$) as the promoter. Preferred embodiments of the transcription factor (24) utilize a fusion that includes at least one light-oxygen voltage (LOV) sensing domain, CRY2, CIB, TULIP, or the phytochrome B (PhyB) and PIF3 binding domains. A more preferred embodiment utilizes EL222. Other preferred embodiments utilize additional domains fused to the transcription factor; for example, the use of a VP16 transcriptional activation domain and a nuclear localization signal (NLS) sequence. These additional domains may be added to the transcription factor at its N or C terminus. With respect to the terminator portion (26), any terminator may be utilized, although preferred embodiments of terminator portion (26) utilize the terminators of CYC1 ($T_{CYC1}$), ACT1 ($T_{ACT1}$), or ADH1 ($T_{ADH1}$).

The second sequence (30) may be used to allow light to control growth, by regulating an enzyme that is essential for growth. For example, in strains of yeast with a triple PDC deletion (pdc1-Δ, pdc5-Δ, and pdc6-Δ), turning off PDC1 expression prevents growth on glucose. Thus, the second sequence (30) comprises a promoter portion (32) and a portion that codes for a metabolic enzyme (34), where the metabolic enzyme (34) is preferably an essential enzyme for growth, such as PDC1, which is essential for growth on glucose in a strain of yeast with a triple PDC deletion. The promoter portion (32) is preferably a sequence that is capable of binding the transcription factor fusions (24), such as $P_{C120}$.

In addition, the second sequence (30) may also be fused to an optional degron domain (36), and may also include a terminator (38). The degron domain (36) preferably utilizes photosensitive degron (PSD) domains, chemically induced degron domains, or constitutively active degron domains.

With respect to the terminator (38), any appropriate terminator may be utilized, although preferred embodiments of terminator (38) utilize the terminators of CYC1 ($T_{CYC1}$), ACT1 ($T_{ACT1}$), or ADH1 ($T_{ADH1}$).

The third sequence (40) comprises a promoter (42), which can be activated by the gene encoded by the first sequence, and further comprises a gene that encodes for a repressor (44). The promoter (42) is preferably a sequence that is capable of binding the transcription factor fusions (24), such as $P_{C120}$. As noted below, the repressor can be used to control the fourth sequence (50); one preferred embodiment utilizes GAL80 as the repressor in a strain in which the endogenous GAL80 gene has been deleted. Similar to the second sequence (30), the third sequence (40) may also include an optional degron (46), and may also include a terminator (48). The degron (36) preferably utilizes photosensitive degron (PSD) domains, chemically induced degron domains, or constitutively active degron domains. With respect to the terminator (48), any appropriate terminator may be utilized, although preferred embodiments of terminator (48) utilize CYC1 ($T_{CYC1}$), ACT1 ($T_{ACT1}$), or ADH1 ($T_{ADH1}$).

The fourth sequence (50) comprises a promoter (52) and a portion that is capable of inducing expression of metabolic enzymes (54). The promoter (52) can be repressed by the repressor encoded by the third sequence (44), activated by a gene encoded by a fifth sequence (60), or both. In more preferred embodiments, the promoter is a GAL1 promoter ($P_{GAL1}$); a strong promoter that is normally activated by Gal4p, if not for the repressor Gal80p.

The portion of the fourth sequence (50) that is capable of inducing expression of at least one metabolic enzyme or protein (54), and is generally selected so as to allow the yeast to overproduce a desired chemical. For example, the expressed metabolic enzyme could be an enzyme that is used for controlling a yeast pathway that produces lactic acid (with for example, the enzyme LDH), or isobutanol, 2-methyl-1-butanol, and/or isopentanol (3-methyl-1-butanol) (with for example, the enzyme Ilv2p). The fourth sequence could also be designed to induce expression of a protein, such as GFP. Similar to the second (30) and third (40) sequences, the fourth sequence (50) may also include an optional degron domain (56), and may also include a terminator (58). The degron domain (56) preferably utilizes photosensitive degron (PSD) domains, chemically induced degron domains, or constitutively active degron domains. With respect to the terminator (58), any appropriate terminator may be utilized, although preferred embodiments of terminator (58) utilize the terminator of CYC1 ($T_{CYC1}$), ACT1 ($T_{ACT1}$), or ADH1 ($T_{ADH1}$).

Figure 2:
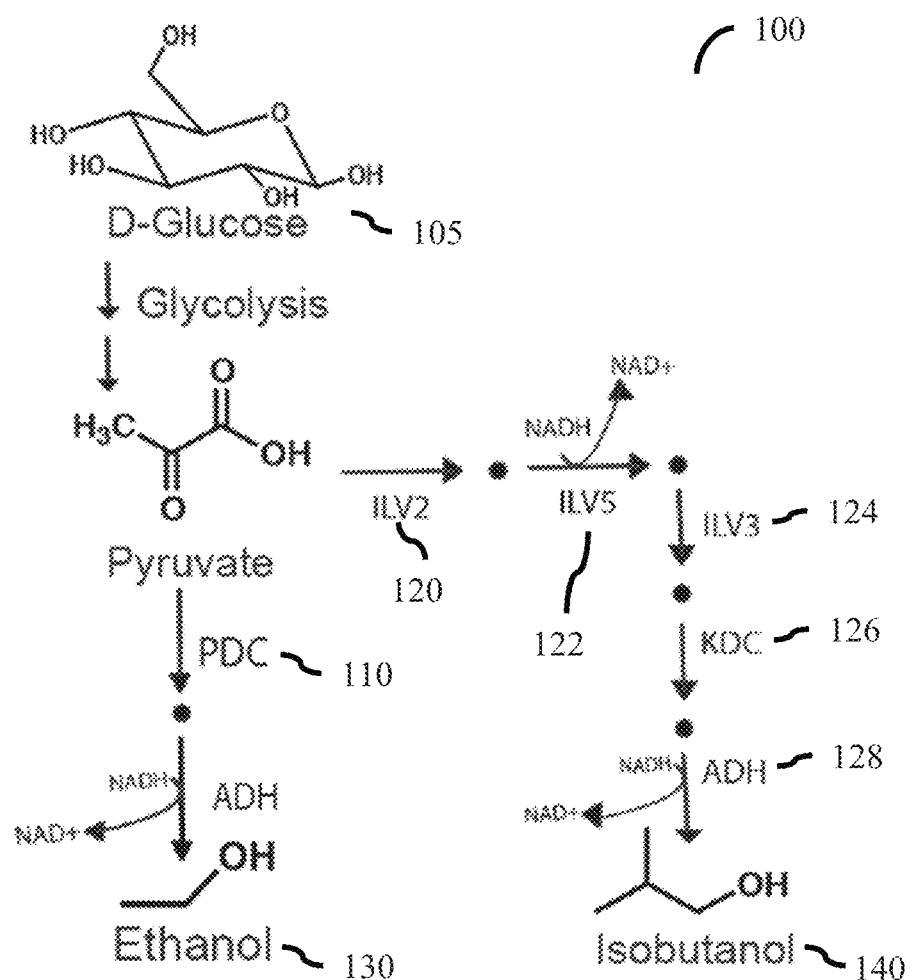
FIG. 2 depicts isobutanol and ethanol metabolic pathways in yeast.

Referring briefly to FIG. 2, the metabolic pathways (100) for yeast are shown that begin with glucose (105) and end in a desired product, isobutanol (140) or an undesired product, ethanol (130). In one embodiment, the fourth sequence (50) is capable of inducing expression of at least one gene encoding a metabolic enzyme that drives the desired metabolic pathway to completion from pyruvate to isobutanol: ILV2 (120), ILV5 (122), ILV3 (124), KDC (126), and ADH (128). In the case illustrated in FIG. 2, the sequence could positively regulate the ILV2 gene (120). For example, the ILV2 gene can be fused to a promoter controlled by a specific nutrient, including but not limited to galactose-regulated promoters such as $P_{GAL1}$ or $P_{GAL10}$. Since Gal4p can activate $P_{GAL1}$, using a $P_{GAL1}$-ILV2 fusion allows Gal4p to be used to positively regulate the expression of ILV2 gene.

As discussed above, if a fifth sequence (60) is utilized, it should encode for an endogenous or exogenous activator (64) expressed by a promoter (62), which could be a constitutive promoter, an inducible promoter, or a gene circuit. Like electronic circuits, a gene circuit is an application of biology whereby biological elements are designed in a way so that the circuit performs logical functions. The logical functions vary greatly, but are inclusive of inducing production of a chemical or adding an element that can be visually detected, such as GFP. In certain embodiments, the activator is Gal4p. In other embodiments, the fifth sequence may also utilize a promoter comprising TEF1 ($P_{TEF1}$), ACT1 ($P_{ACT1}$), ADH1 ($P_{ADH1}$), PGK1 ($P_{PGK1}$), or TDH1 ($P_{TDH1}$). Similar to the second (30), third (40), and fourth (50) sequences, the fifth sequence (60) may also include an optional degron domain (66), and may also include a terminator (68). The degron domain (66) preferably utilizes photosensitive degron (PSD) domains, chemically induced degron domains, or constitutively active degron domains. With respect to the terminator (68), any appropriate terminator may be utilized, although preferred embodiments of terminator (68) utilize the terminator of CYC1 ($T_{CYC1}$), ACT1 ($T_{ACT1}$), or ADH1 ($T_{ADH1}$).

Assembly of DNA Constructs

Promoter-gene-terminator sequences were cloned into standardized vector series (pJLA vectors, Avalos et. al. 2013). Doing so allowed for easy manipulation and generation of multi-gene plasmids. All genes were designed to have NheI and XhoI restriction sites at the 5' and 3' ends, respectively, which were used to insert the genes into pJLA vectors. Each promoter-gene-terminator construct is flanked by XmaI and AgeI restriction sites at their 5' ends, and MreI, AscI and BspEI sites at their 3' ends, which were used for easy assembly of multi-gene plasmids as previously described (Avalos et al. 2013) (See Supplementary Table 1).

All cloning was done using standard protocols and kits. Qiagen Miniprep, Qiagen Gel Extraction, and Qiagen PCR purification kits were used to extract and purify plasmids and DNA fragments. Most genes and promoters (ILV2, ILV3, ILV5, ARO10, AdhA-RE1, GAL4, GAL80, $P_{GAL1}$, $P_{TEF}$, $P_{TDH3}$, $P_{PGK1}$, $P_{CYC1}$, $P_{ADH1}$, GFP) were amplified from yeast genomic DNA or lab plasmids, using the Phusion® High-Fidelity DNA Polymerase from NEB, following manufacturer's instructions. More genes were amplified from plasmids sent to us by other groups: PsLDH from Dr. Jinsuk J. Lee (Lee 2015) and the photosensitive degron derived from the fusion of phototropin1 LOV2 domain (with V19L mutation) from *Arabidopsis thaliana* and a synthetic degradation sequence derived from the murine ornithine decarboxylase (ODC) from Dr. Christof Taxis (Usherenko 2014). Some sequences ($P_{C120}$, VP16-EL222) were purchased as g-blocks from IDT or synthesized by Bio Basic's gene synthesis service. When pJLA vectors were not available, Gibson isothermal assembly was used to produce the constructs, based on the protocols of the Megason lab at Harvard (Gibson Smith 2009). Enzymes were purchased from NEB (XmaI, AscI, NheI, XhoI, BspEI, AgeI, T4 DNA ligase, Phusion Polymerase) and Thermo Fischer (MreI).

Figure 22:
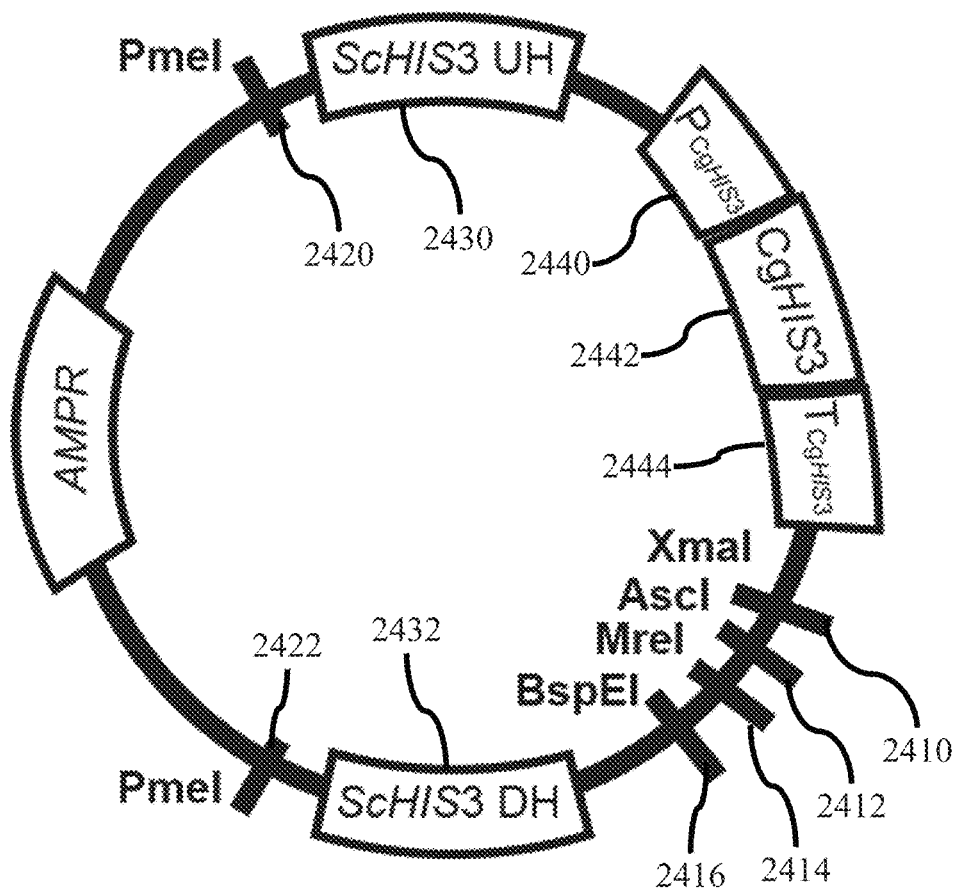
FIG. 22 depicts a HIS3 integration vector used for cloning circuits into yeast.

As shown in FIG. 22, the single copy integration plasmid pNH603 (Hyun Youk and Wendell A. Lim 2014) was modified to make a plasmid compatible with the pJLA vectors that can be used to introduce gene cassettes into the HIS3 locus. The AscI site of pNH603 was first removed and the $T_{ADH1}$ sequence between PtsI and SacI replaced with a fragment containing an XmaI restriction site. Subsequently, a cloning sequence array was introduced consisting of XmaI (2410), AscI (2412), MreI (2414), and BspEI (2416) between the XmaI site (contained in the sequence that replaced the $T_{ADH1}$) and KpnI restrictions sites, to make pYZ12-B. This addition makes pYZ12-B compatible with the pJLA platform of vectors, and allowed for easy transfer of gene cassettes from pJLA 2μ plasmids. Gene constructs in pYZ12-B were integrated into the HIS3 locus by linearizing the plasmid with PmeI (2420, 2422). Genes in a single copy episomal plasmid (CEN) were introduced using pRSII416; cassettes comprised of promoter (2440)-gene (2442)-terminators (2444) were inserted into pRSII416 by cutting out gene constructs from pJLA vectors with XmaI and MreI and inserting at the XmaI site of pRSII416.

Figure 23:
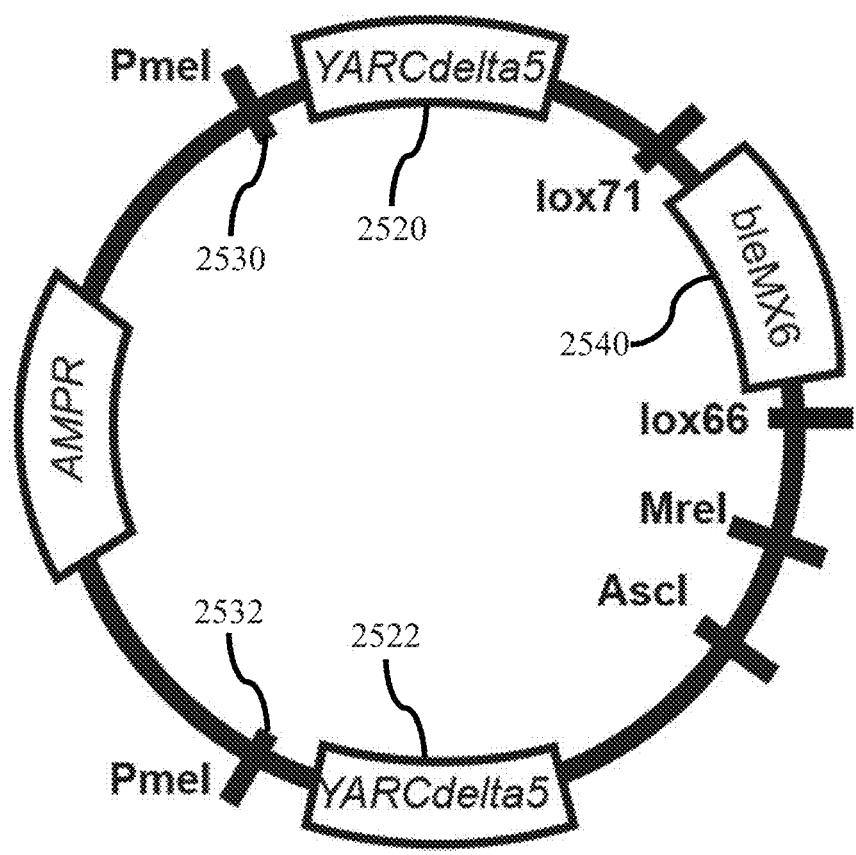
FIG. 23 depicts a delta integration vector used for cloning circuits into yeast.

Similar to pYZ12-B, and as shown in FIG. 23, a plasmid, pYZ23, was developed to integrate multiple copies of gene constructs into the δ-sites of the yeast genome, where pYZ23 is compatible with pJLA vectors (Supplementary Table 1). The delta site targeted for multicopy genomic integration is YARCdelta5, the 337 bp long terminal repeat (LTR) of *Saccharomyces cerevisiae* Ty1 retrotransposons (YARCTy1-1, SGD ID: S000006792). The delta integration vector pYZ23 was constructed with four overlapping DNA fragments using Gibson isothermal assembly pYZ12-B, containing (1) the AMPR gene; (2) the first 207 bp; (3) the last 218 bp of YARCdelta5 LTR, which were amplified from the BY4741 genome using primer pairs Yfz_Oli39 and Yfz_Oli40, and Yfz_Oli43 and Yfz_Oli44, respectively; and (4) the BleMX6 gene cassette from pCY 3090-07 (Addgene plasmid #36232), amplified with primers Yfz_Oli41 and Yfz_Oli42, which add flanking loxP sites (lox66 and lox71) to the BleMX6 gene. Additional restriction sites including KpnI, AscI, MreI and BspEI were introduced for subcloning.

All vectors were sequenced with Sanger Sequencing before using them to transform yeast.

Yeast Transformations

Yeast transformations were carried out using standard lithium acetate protocols, and the resulting strains are cataloged in Supplementary Table 2. Gene constructs in pYZ12-B and pYZ23 were genomically integrated into the HIS3 locus and δ-sites, respectively, by linearizing the vectors with PmeI, followed by purification using the Qiagen PCR purification kit. Gene deletions were carried out by homologous recombination. DNA fragments containing antibiotic resistance cassettes flanked with Lox-P sites were amplified with PCR from pAG26 (containing the hygromycin resistance gene HygB-phosphotransferase), pUG6 (containing the G418 resistance gene KanMX), or pAG36 (containing the nourseothricin resistance gene NATO, using primers with 40 base pairs of homology to the promoter and terminator regions of the gene targeted for deletion. Antibiotic resistance markers were subsequently removed by expressing Cre recombinase from the pSH62 (AF298785) vector (Güldener U, Heinisch J, Köhler G J, Voss D, Hegemann J H. Nucleic Acids Research 2002; 30, e23). After transformation, cells were plated on synthetic complete (SC) drop out media depending on the autotrophy restored by the construct. In the case of antibiotic selection, cells were plated onto nonselective YPD plates for 16 hours, and then replica plated onto YPD plates with 300 ug/mL hygromycin (purchased from Invitrogen), 200 ug/mL nourseothricin (purchased from Sigma), or 200 ug/mL G418, purchased from Gibco by Life Technologies). Zeocin was used to select for δ-integration ranging from 800 to 1200 ug/mL (purchased from Thermo Fisher Scientific).

All strains with genomic integrations or gene deletions were genotyped with PCR to confirm their accuracy.

Yeast Cell Culture Growth, Centrifugation, and Optical Measurements

Unless otherwise specified, liquid yeast cultures were grown in 24-well plates, at 30° C. and shaken at 200 rpm, in either YPD or SC-dropout media with 2% glucose. When cells were grown under light, blue LED panels (HQRP New Square 12" Grow Light Blue LED 14 W) were placed 40 cm from cell cultures. To control light duty cycles, the LED panels were regulated with a Nearpow Multifunctional Infinite Loop Programmable Plug-in Digital Timer Switch.

Fluorescence and optical density (OD600) measurements were taken using a TECAN plate reader (infinite M200PRO). The excitation and emission wavelengths used for GFP fluorescence measurements were 485 nm and 535 nm, respectively, using an optimal gain for all measurements. The background fluorescence from the media was first subtracted from values. Then, the GFP/OD$_{600}$ values of cells lacking a GFP construct were subtracted from the fluorescence values (GFP/OD$_{600}$) of each sample to normalize for light bleaching of the media and cell contents. All optical density measurements were taken at 600 nm, using media (exposed to the same conditions as the yeast) as blank.

Cell cultures were centrifuged in a table-top centrifuge, using a rotor with 24-well plate adaptors. Unless otherwise specified, plates were centrifuged at 1000 rpm for 10 min.

Construction of OptoEXP System

Figure 3:
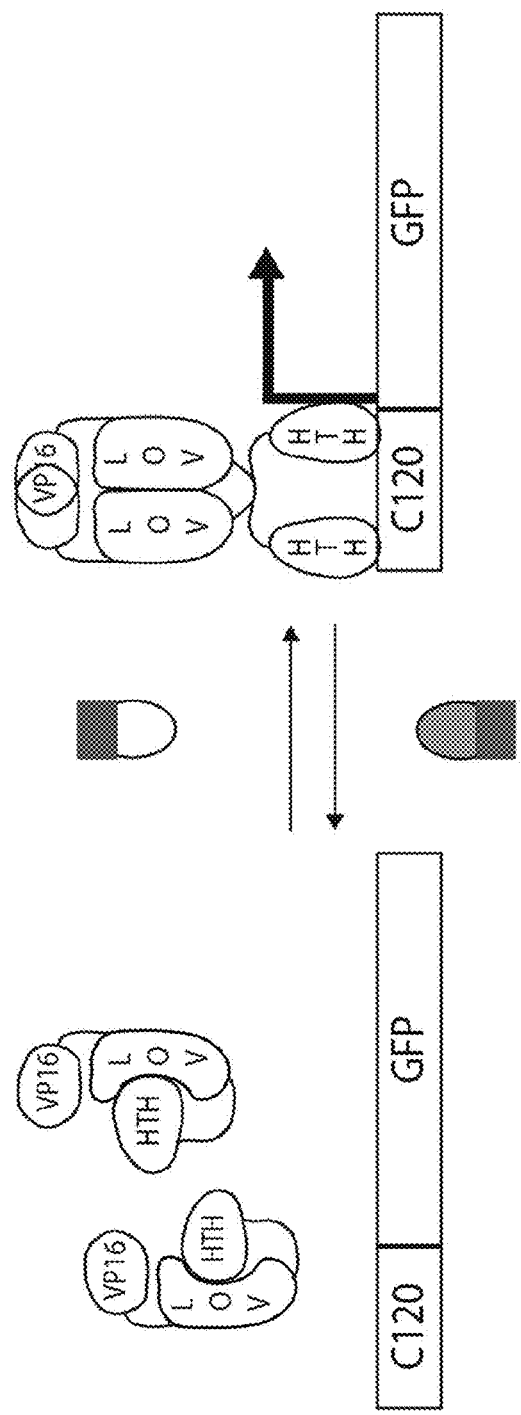
FIG. 3 depicts a VP16-EL222 light inducible gene expression system.

As shown in FIG. 3, the VP16-EL222 light inducible gene expression system was adapted to make an optical gene expression system (OptoEXP) in S. cerevisiae. This system had previously been used in mammalian cells (Motta-Mena 2014), zebrafish, and E. coli (Jayaraman 2016, Nash PNAS 2011, Rivera-Cancel Biochem 2012).

To achieve this, a cassette containing the VP-EL222 transcription factor under the strong constitutive TEF1 promoter ($P_{TEF1}$) and green fluorescent protein (GFP) under $P_{C120}$—the promoter activated by VP-EL222 upon light stimulation—was integrated in the HIS3 locus of a CENPK2-1C yeast strain, resulting in strain YEZ139.

A g-block (IDT) was purchased containing the yeast codon-optimized sequence of VP16-EL222, flanked by NheI and XhoI restriction sites, which were used to insert this gene between a $P_{TEF1}$ promoter and $T_{CYC1}$ terminator, in a plasmid derived from pYZ12-B, (which allows single-integration in the HIS3 locus) to make plasmid EZ_L158. In addition, the C120 and minimal promoter sequence (TAGAGGGTATATAATGGAAGCTCGACTTCCAG), otherwise known as $P_{C120}$, were synthesized using BioBasic's gene synthesis service and created new pJLA vectors with the $P_{C120}$ promoter and either an ADH1 or ACT1 terminator, making pJLA1X1$^{0803}$ and pJLA1X1$^{0802}$, respectively (Supplementary Table 1).

Plasmid EZ_L83 (pJLA111-GFP$^{0803}$) was then built, placing GFP under $P_{C120}$ transcriptional control in a CEN/ARS plasmid with a URA3 marker. EZ_L105 was used to integrate a single copy of $P_{TEF1}$-EL222-VP16-$T_{CYC1}$ construct into the HIS3 locus of CENPK2-1C, selecting strain YEZ24 from a SC-His+2% glucose plate. Subsequently, YEZ24 was transformed with EZ_L83, and selected strain YEZ32 from a SC-Ura+2% glucose plate. In order to benchmark the combination of $P_{TEF1}$-EL222-VP16-$T_{CYC1}$ and a single integrated copy of $P_{C120}$, which is referred to as OptoEXP, the combination was compared to several constitutive promoters expressing GFP. To achieve this, pJLA111-GFP constructs (CEN/ARS with URA3 markers) were made containing $P_{CYC1}$ (EZ_L64), $P_{ADH1}$ (EZ_L63), $P_{PGK1}$ (EZ_L67), $P_{GPD1}$ (EZ_L65), and $P_{TEF1}$ (EZ_L66), which were used along with pRSII416 (empty plasmid control) to transform YEZ24 to make yeast stains YEZ28 (EZ_L64), YEZ28 (EZ_L63), YEZ29 (EZ_L67), YEZ30 (EZ_L65), YEZ31 (EZ_L66), and YEZ32C (pRSII416).

To test these strains, cells were grown overnight in the dark under tinfoil. Four different colonies were tested for each transformation. After growing in the dark overnight, cells were diluted to 0.1 OD$_{600}$, placing 1 mL of each cell culture into individual wells of a 24-well costar plate. Five identical plates were prepared and one was tin-foiled. The plates were then placed under either constant blue light or blue light under duty cycles of 5 s ON/75 s OFF, 8 s ON/72 s OFF, and 11 s ON/69 s OFF. Duty cycles were used instead of light intensity to better control light dose and reproducibility. Cell cultures were grown for 8 hours under blue light panels as described before. YEZ24 was used as a control for no GFP production. Error bars represent one standard deviation from biological replicates (n=4).

Figure 4:
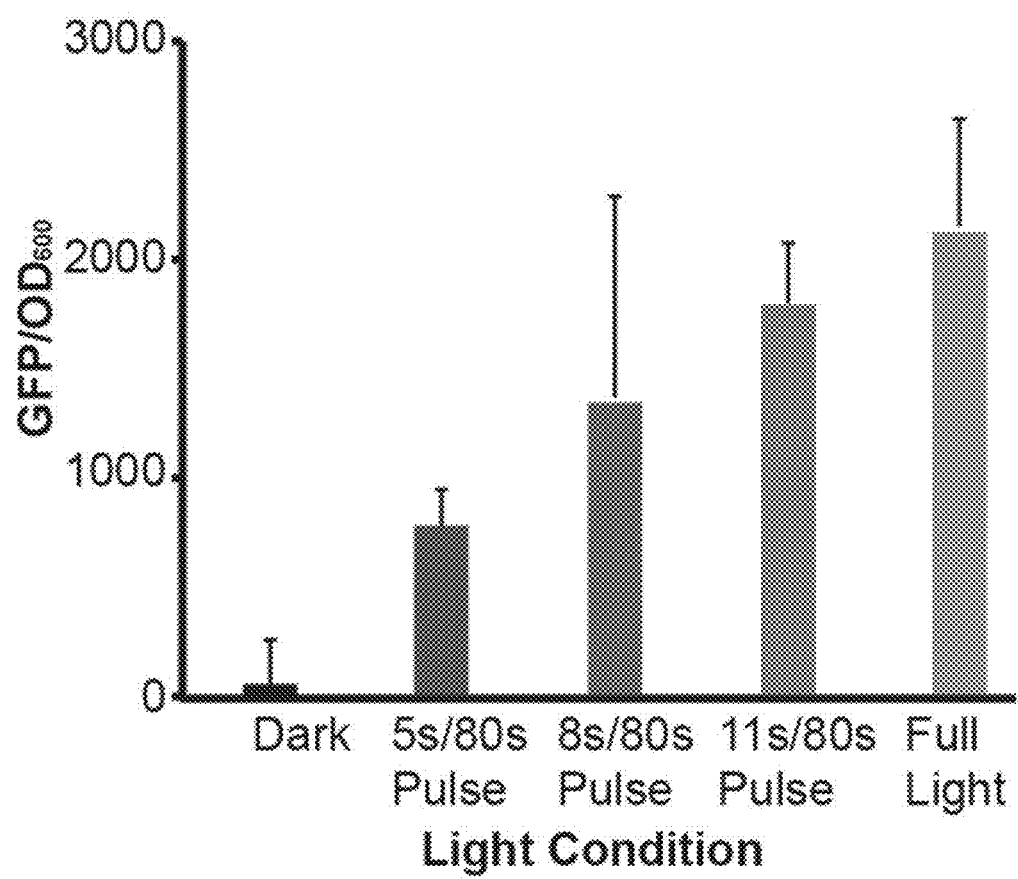
FIGS. 4 and 5 are graphs of GFP expression levels of strains containing one embodiment of the OptoEXP system.

Measuring the levels of GFP expression in YEZ139 as a function of light exposure, revealed the ability to tune expression levels from $P_{C120}$ by controlling light duty cycle. FIG. 4 shows a comparison of the GFP fluorescence of YEZ139 grown in either the dark or full blue light, as well as intermediate duty cycles of light. The expression of GFP has a maximal fold change of 43 from dark to light and tunable activation controlled by light duty cycle.

Figure 5:
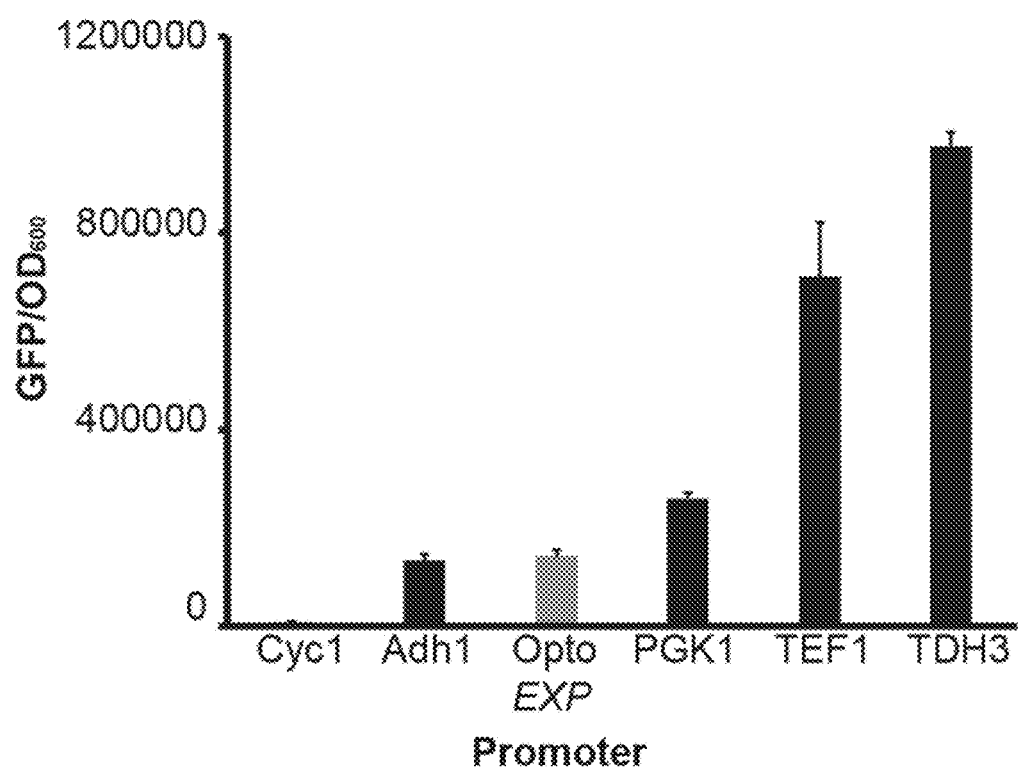

FIG. 5 shows the maximum expression of GFP achieved by this ($P_{C120}$-GFP) construct compared to the GFP expression levels from strong constitutive promoters commonly used in yeast metabolic engineering. The maximum activation levels of OptoEXP are comparable to the levels reached constitutively by the promoter of the alcohol dehydrogenase ADH1 ($P_{ADH1}$), which is at the lower end in strength of the constitutive promoters commonly used in metabolic engineering. However, this relatively weak level of expression can be overcome by integrating multiple copies of the $P_{C120}$-GFP construct.

Construction of the OptoINVRT Circuits

Although in principle OptoEXP is enough to separate a growth phase from a production phase of fermentation, a second transcriptional program can be simultaneously implemented by using an optogenetic circuit that inverts the response to light, similar to the NOT logical gate required for many digital processes. Thus, a class of optogenetic circuits was developed, hereinafter referred to as Opto-INVRT, which represses genes in blue light, and induces them in the dark.

Figure 6:
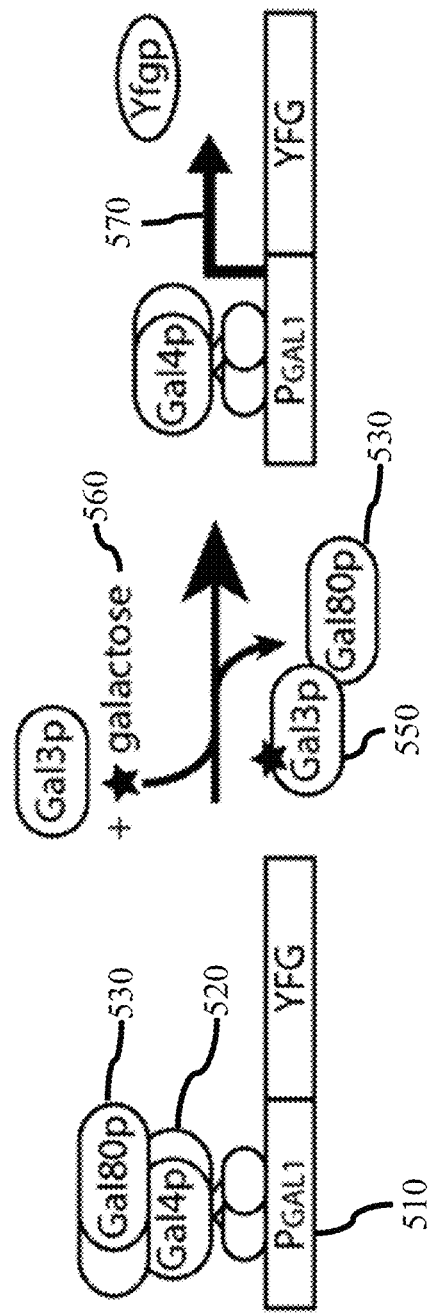
FIG. 6 depicts the interaction between Gal4p, Gal80p, and a GAL1 promoter.

To build this example of an OptoINVRT circuit, the gene regulatory mechanism of yeast galactose (GAL) metabolism was harnessed. These circuits work by optically regulating the interaction between the transcription factor Gal4p and the repressor Gal80p on the activity of GAL1 promoter ($P_{GAL1}$). As illustrated in FIG. 6, $P_{GAL1}$ (510) is a strong promoter activated by Gal4p (520), and would be constitutively active (570) in glucose if it was not for the repressor Gal80p (530). In wild-type strains Gal80p repression is removed by Gal3p bound to galactose (which is the inducer). Placing GAL80 under $P_{C120}$, in a gal80-Δ strain, and in the presence of constitutive GAL4 expression, light-dependent repression of $P_{GAL1}$ can be induced.

Starting from strain, YEZ44, in which both GAL80 and GAL4 are deleted, a cassette containing $P_{TEF1}$-VP-EL222, $P_{GAL1}$-GFP, $P_{ADH1}$-GAL4, and two copies of $P_{C120}$-GAL80 was introduced. This gene circuit is referred to as Opto-INVRT1, which was integrated in the HIS3 locus of YEZ44 to produce YEZ100 (Supplementary Table 2).

Conceptually, a general mode of operation is shown pictorially in FIGS. 7A-7D. To place GAL80 expression under light control, two copies of GAL80 (612) were reintroduced under the control of $P_{C120}$ (610) in a YEZ44 strain, and integrated EL222 under the strong constitutive $P_{TEF1}$ promoter. A GFP reporter (622) was used under the control of $P_{GAL1}$ (620) to characterize the strength and light-sensitivity of the OptoINVRT1 circuit. As shown in FIGS. 7A and 7B, when the light (605) is activated, Gal80p is produced, which reduces Gal4p transcription of GFP (622). However, as shown in FIGS. 7C and 7D, when the light (607) is turned off, Gal80p is not produced, which enhances Gal4p transcriptional activation of GFP (620).

Other variations in OptoINVRT circuit design are also envisioned, which might be useful for different metabolic engineering applications. For example, changing the promoter driving GAL4 to the stronger constitutive promoter $P_{PGK1}$ was considered, and is referred to as OptoINVRT2. In addition, a photosensitive degron domain (PSD) (Usherenko 2014) was fused to the C-terminus of Gal4p, which induces protein degradation upon light stimulation. When combined with expression of GAL4-PSD from $P_{PGK1}$, this variation is referred to as OptoINVRT3. Integrating OptoINVRT2 and OptoINVRT3 in the HIS3 locus of YEZ44 to make YEZ101 and YEZ102, respectively, and using $P_{GAL1}$-GFP as a reporter, significant differences are found between the three circuits (Supplementary Table 2 and 4).

These OptoINVRT circuits were initially developed and characterized in two yeast strain backgrounds: The first is YEZ44, which is CENPK.2-1C with gal80-Δ, gal4-Δ deletions. The second strain background is Y202, which is Y200, a BY4741 derivative, with a gal80-Δ deletion (Supplementary Table 2).

Gene circuits were assembled using restriction enzyme digests and ligations afforded by pJLA vector system, in which ORFs were inserted using NheI and XhoI sites, and multiple cassettes assembled using XmaI (or AgeI), MreI (or BspEI), and AscI. Each gene circuit is comprised of five promoter-gene-terminator cassettes ($P_{TEF1}$-VP16-EL222-$T_{CYC1}$, two copies of $P_{C120}$-GAL80-$T_{ACT1}$, $P_{GAL1}$-GFP-$T_{ADH1}$, and $P_{ADH1}$- or $P_{GK1}$-GAL4-$T_{ADH1}$). Each gene circuit was constructed by integrating five promoter-gene-terminator sequences in the HIS3 locus (Supplementary Table 3). The photosensitive degron (PSD) used in Opto-INVRT3 is the V19L variant designed using a LOV2 domain from *Arabidopsis thaliana* with a synthetic degradation sequence called cODC1 from the carboxy-terminal degron of murine ornithine decarboxylase (ODC) on the C-terminus, previously described (Usherenko 2014). This PSD was fused to the C-terminus of GAL4 using Gibson assembly by cutting with XhoI and using overhangs with GAL4 and $T_{ACT1}$ (sequence in supplementary sequences). The three OptoINVRT circuits, controlling GFP expression, were initially characterized by transforming YEZ44 to produce YEZ100 (OptoINVRT1), YEZ101 (OptoINVRT2), and YEZ102 (OptoINVRT3) and Y202 to produce YEZ115 (OptoINVRT1), YEZ116 (OptoINVRT2), and YEZ117 (OptoINVRT3) (Supplementary Table 2). OptoINVRT circuits were characterized using strains YEZ100-102 and YEZ115-117 by performing the same experiment performed on YEZ32 described above to characterize the OptoEXP system. In this case, cells were exposed to full light, complete darkness, or light pulses of 8 s On/72 s Off.

The circuits were transformed into YEZ44 (YEZ100, 101, 102) and Y202 (YEZ115, 116, 117) for testing the inversion of these repressible circuits from light to darkness, crucial for the adaptation of this technology into metabolic engineering as a metabolic switch. The same experiment as the one designed to test the OptoEXP system was performed. Light was only pulsed at 8 s On/72 s Off in order to determine the effectiveness of the circuit at low induction of Gal80p.

YEZ31 and YEZ29 were also measured, which had TEF1 driving GFP and PGK1 driving GFP respectively—these controls had negligible variation throughout the course of the experiment or as a function of light. To test these strains, multiple colonies were pooled and grown overnight in 1 mL media. After 10 hours, the colonies were diluted 1:4, and then plated on 6 24-well plates, with 4 samples of each strain per plate. Then 3 of the plates were wrapped in tin foil, and placed on the shaker in the dark, while the other 3 plates were placed in the shaker under blue light. Every hour, a measurement was taken of one light plate, one dark plate, minimizing the time each plate was out of the incubator. The fluorescence and the $OD_{600}$ were measured using a Tecan plate reader. Media-blanks were also included on each plate to act as fluorescence and OD controls.

Figure 8A:
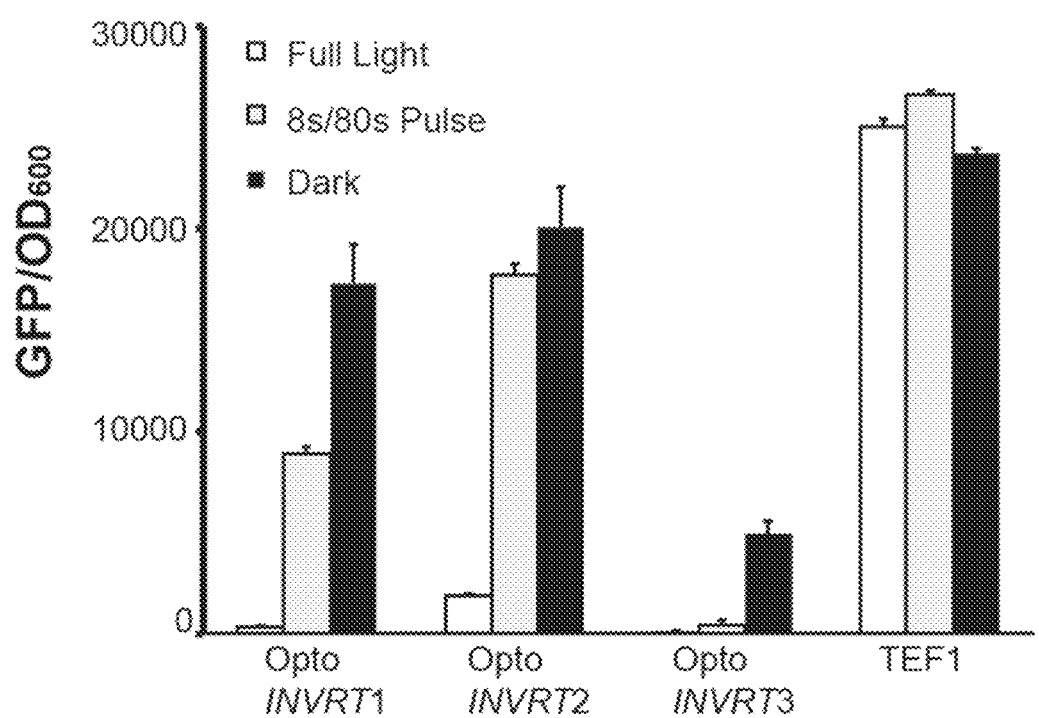
FIGS. 8A, 8B, and 8C are graphs of GFP expression levels of strains containing embodiments of OptoINVRT circuits.

As seen in FIG. 8A, when YEZ100 is grown in the dark the OptoINVRT1 circuit exhibits high GFP expression, equivalent to 70% of $P_{TEF1}$ levels, a strong promoter used in metabolic engineering. However, when grown in blue light, a 45.7-fold decrease in GFP signal was observed, demonstrating that OptoINVRT1 acts as a highly efficient photoswitchable repressor.

While OptoINVRT1 was an effective inverter that can be used in parallel with the direct OptoEXP system, additional variations were explored in the OptoINVRT circuit design, as circuits with different fold change, sensitivities, and maximum levels of expression might be useful for different metabolic engineering applications. Altering the level of expression and protein stability of Gal4p was tested to determine whether that could tune the expression levels of $P_{GAL1}$-GFP in the lit and dark states. As described above, first the promoter driving GAL4 was changed to the stronger constitutive promoter $P_{PGK1}$ to make OptoINVRT2. Second, a photosensitive degron domain (the V19L variant of the degron designed using a LOV2 domain from *Arabidopsis thaliana* with a synthetic degradation sequence called cODC1 from the carboxy-terminal degron of murine ornithine decarboxylase (ODC) on the C-terminus) was attached to the C-terminus of Gal4p to induce its degradation upon light stimulation, and improve the fold-change between lit and dark states to make OptoINVRT3.

In this circuit, light stimulation would inhibit Gal4p through two independent processes—Gal4p degradation (by the PSD) and Gal4p-Gal80p binding (by expression of GAL80)—to increase light-mediated repression of $P_{GAL1}$-activated genes. This change was incorporated in the context of stronger $P_{PGK1}$-GAL4 production, naming the resulting circuit OptoINVRT3.

OptoINVRT1, OptoINVRT2 and OptoINVRT3 circuits were integrated in YEZ44, to make strains YEZ100, YEZ101, YEZ102, respectively. As shown in FIG. 8A, the stronger $P_{PGK1}$ promoter driving the expression of GAL4 in OptoINVRT2 resulted in a slightly higher GFP expression in the dark than OptoINVRT1, reaching 85% of $P_{TEF1}$, but it also results in a more leaky circuit, with only an approximately 11-fold difference in GFP expression between the lit and dark conditions.

As expected, OptoINVRT3 showed a substantially higher fold change of GFP expression (more than 70-fold) from light to dark, compared to OptoINVRT1 or OptoINVRT2, likely due to the synergy of light-induced GAL80 expression and Gal4p degradation. However, this comes at the expense of lower maximum expression of GFP in the dark, about 21% of $P_{TEF1}$, probably due to reduced stability or activity of the Gal4p-PSD fusion protein. These circuits also exhibited a wide range of differences in light sensitivity. OptoINVRT3 has the highest light sensitivity (more than 90% of maximum repression with 10% light dose), while OptoINVRT2 is the most refractory circuit (only 12% repression with 10% light dose).

Figure 21:
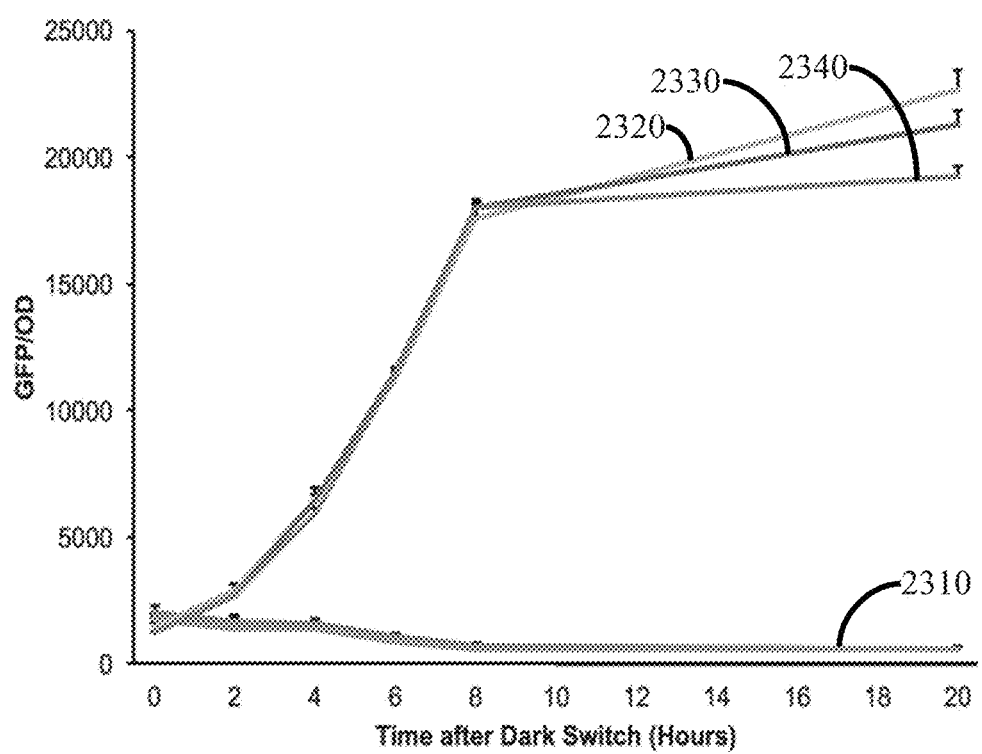
FIG. 21 is a graph illustrating the light-to-dark-kinetics of strains containing GFP under the control of OptoINVRT1, 2, and 3.

The three different OptoINVRT circuits show similar dark induction kinetics. Samples of YEZ100, YEZ101, YEZ102 were grown in blue light (continuous repression) from OD of 0.1 to OD 3, and some were then switched to darkness. GFP expression was measured through time. As shown in FIG. 21, for those samples placed in the dark YEZ100 (2320), YEZ101 (2330), and YEZ102 (2340), the system begins to reverse instantly (2310). Error bars represent standard deviations of 1 mL biological culture replicates exposed to the same light conditions (n=4).

Figure 8B:
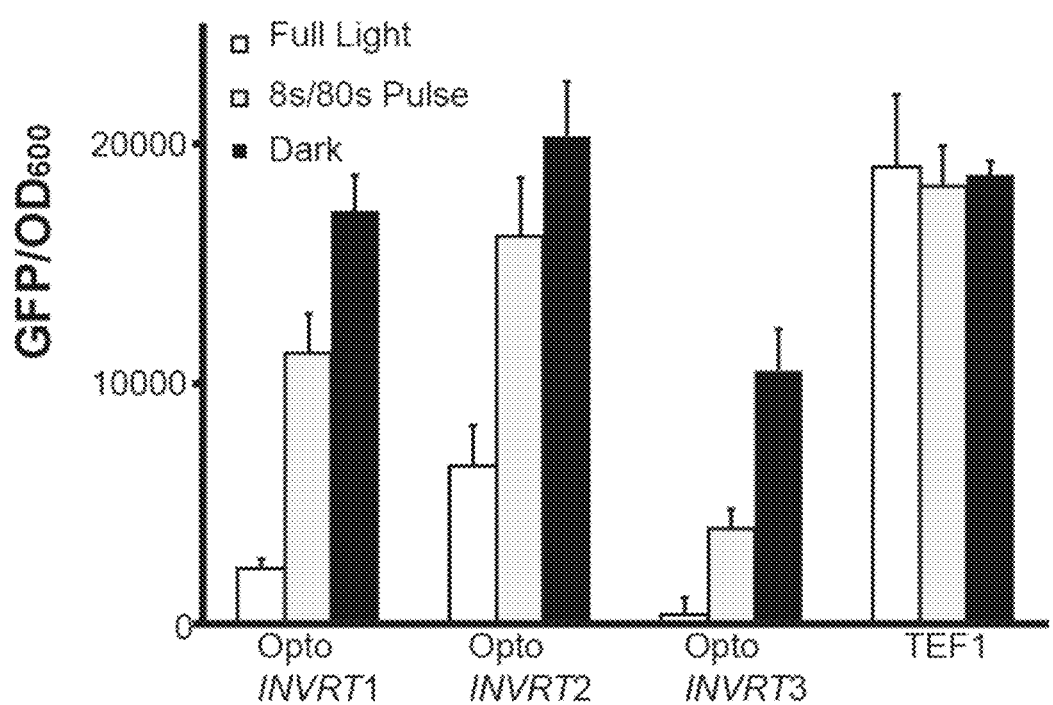

The circuits show similar light responses in a different strain background later used for metabolic control, Y202, in which the three endogenous pyruvate decarboxylases (PDC1, PDC5, PDC6) and GAL80 are deleted from a S288C-derived strain (See FIG. 8B). The results indicate that this platform can achieve a wide range of expression levels, light sensitivities and fold-change responses for flexible incorporation in diverse metabolic engineering applications.

Again, the three example circuits behave differently from each other due to differences Gal4p expression, stability, and activity. The stronger constitutive promoter ($P_{PGK1}$) driving GAL4 expression in OptoINVRT2, compared to that in OptoINVRT1 ($P_{ADH1}$), gives rise to higher constitutive levels of Gal4p in cells carrying OptoINVRT2. This results in slightly higher maximum GFP expression in full dark (85% of $P_{TEF1}$) of genes controlled by OptoINVRT2, but also a higher background expression in full light, compared to OptoINVRT1 (See FIG. 8A).

Because of this difference, even though the maximum expression levels attained with both circuits is similar, the fold of gene induction achievable with OptoINVRT1 is much higher (40-fold) than that with OptoINVRT2 (10-fold). In addition, the lower levels of Gal4p in cells carrying OptoINVRT1 makes this circuit more sensitive to light, and is able to repress GFP by 50% with only 10% of light exposure (⅞₀ seconds duty cycle). On the other hand, OptoINVRT2 only shows 12% of repression with the same light dose. OptoINVRT3 uses the same strong promoter driving GAL4 expression as OptoINVRT2 ($P_{PGK1}$), but the gene product Gal4p is fused to a photosensitive degron domain, which reduces the stability of Gal4p when exposed to blue light. This makes OptoINVRT3 the circuit with the highest fold of gene induction (70-fold). It also makes OptoINVRT3 the most sensitive circuit, capable of achieving 90% gene repression with only 10% of light exposure. However, as shown in FIGS. 8A and 8B, the maximum level of gene expression achieved with OptoINVRT3 is only about a fourth of that achieved with the other two circuits (20% $P_{TEF1}$), probably due to increased instability of Gal4p even in the dark (due to leakiness of the degron photoactivation), reduced activity of the Gal4p-PSD fusion, or both.

Therefore, if the specific application requires maximum gene expression or a refractory circuit that will keep genes induced even with short light exposures (e.g. unintended light leaks) then of the three example circuits, OptoINVRT2 is likely the best option. If the application requires a tighter gene repression in full light but still high levels of maximum gene expression, or a more sensitive circuit that can significantly repress a gene with short light pulses, then OptoINVRT1 would be most recommended. Finally, if the application requires a very low background gene expression or the ability to strongly repress genes with only short pulses of light then OptoINVRT3 would probably be the circuit of choice.

The initial characterization of the OptoINVRT circuits was done in a CEN.PK2 strain with a double gal4-Δ, gal80-Δ gene deletion (YEZ44). However, when these circuits were tested in a metabolic engineering application, a preexisting triple pdc (pdc1-Δ, pdc5-Δ, pdc6-Δ) knockout S288C strain with only gal80-Δ deletion (Y202) was used. An inability to delete GAL4 from this strain suggests it might be essential in this genetic background. To address this shortcoming, the OptoINVRT circuits were characterized again in Y202 (making strains YEZ115, YEZ116, and YEZ117, respectively). Most of the overall trends of the OptoINVRT circuits seen in CEN.PK2 still hold in this S288C GAL4-containing strain with a few notable exceptions. All three circuits had a higher background gene expression in the light and, consequentially, a reduced overall fold of induction (Supplementary Table 4). In addition, the maximum level of gene expression in the dark was significantly increased in all OptoINVRT circuits (FIG. 8B). The sensitivities of Opto-INVRT1 and OptoINVRT3 were also reduced. These effects may be attributed in part to differences in genetic background between CEN.PK2 and S288C, but the most likely explanation is the endogenous GAL4 that remains in Y202 (the S288C-derived strain). GAL4 is constitutively expressed in glucose under normal circumstances (Griggs Johnston 1991), so increased levels of Gal4p in Y202-derived strains can explain most of the differences observed. The significant differences between OptoINVRT3 in YEZ44 and Y202 suggest that the endogenous Gal4p is interacting with the Gal4p-PSD degron fusion. Gal4p acts as a dimer, so it is possible that dimers of wild type and fusion Gal4p proteins form in OptoINVRT3, increasing the effective activity of Gal4p-PSD in Y202.

Other variants of OptoINVRT circuits are envisioned. For example, in some embodiments, the GAL80 may have a degradation sequence attached to it so the circuit turns on more quickly in the dark. Many degradation domains are envisioned for this, which may include but is not limited to a PEST sequence, such as a CLN2 PEST tag having the sequence ASNLNISRKLTISTPSCSFENSNSTSIPSPASSSQSHTPMRNMSSLSDNSVFSRNMEQSSPIT PSMYQFGQQQSNSICGSTVSVNSLVNTNNKQRI-YEQITGPNSNNATNDYIDLLNLNESNKENQNPA-TAHYLNGGPPKTSFINHGMFPSPTGTINSGKSSSAS-SLISFGMGNTQVI; a CL1 mutant tag having the sequence ACKNWFSSLSAFVIAL; or a ornithine decarboxylase (ODC) derived sequence, such as an ODC mutant tag having the sequence: FPPEVEEQDDGTLPMSCAQESGMDRH-PASCPERAAcASARINV. In some embodiments, promoters are also modified, which may include but is not limited to altering the GAL1 promoter ($P_{GAL1}$) by either deleting a Mig1p-binding site and/or by adding extra Gal4p-binding sites. Examples of these $P_{GAL1}$ mutants can be seen in the following sequences: (1) agctggagctcaccggtatacccgggCG-GATTAGAAGCCGCCGAGCGGGTGACAGCCCTCC GAAGGAAGACTCTCCTCCGTGCGTCCTCGTCTT-CACCGGTCGCGTTCCTGAAACGCAGATG TGCCTCGCGCCCGCACTGCTCCGAACAATAAAGAT-TCTACAATACTAGCTTTTATGGTTATGAAGAG-GAAAAATTGGCAGTAACCTGGTTGGTAAAACCTT-CAAATGAACGAATCAAATTAACAACC ATAGGATGATAATGCGATTAGTTTTTTAGCCTTATTT-TAGTAGTAATTAATCAGCGAAGCGATGATTTTT-GATCTATTAACAGATATATAAATGCAAAAAC TGCAT-AACCACTTTAACTAATACTTTCAACATTTTCGGT TTGTATTACTTCTTATTCAAATGTAATAAAAGTAT-CAACAAAAAATTGTTAATATACCTCTATACTT-TAACGTCAAGGAGAAAAAACTATAgcggccgc TAAAATCATGGC; and (2) agctcaccggtatacccgggCG-GATTAGAAGCCGCCGAGCGGGTGACAGCCCTCC GAAGGAAGACTCTCCTCCGTGCGTCCTCGTCTT-CACCGGTCGCGTTCCTGAAACGCAGATGTGCCT CGCGCCGCACTGCTCCGAACAATAAAGATTCTA-CAATACTAGCTTTTATGGTTATGAAGAGGAAAAAT-TGGATGATTTTTGATCTATTAACAGA-TATATAAATGCAAAAACGG ATTAGAAGCCGCCGAGCGGGTGACAGCCC TCCGAAGGAAGACTCTCCTCCGTGCGT CCTCGTCTTCACCGGTCGCGTTCCTGAAACGCA-GATGTGCCTCGCGCCGCACTGCTC CGAACAATAAAGATTCTACAATACTAGCTTT-TATGGTTATGAAGAGGAAAAATTGGC AGTAACCTGGTTGGTAAAACCTTCAAAT-GAACGAATCAAATTAACAACCATAGGAT GATAATGCGATTAGTTTTTTAGCCTTATTT-TAGTAGTAATTAATCAGCGAAGCGATGATTTTT-GATCTATTAACAGATATATAAATGCAAAAACTGCAT-AACCACTTTAACTAA TACTTTCAACATTTTCGGTTTGTATTACTTCTTATT-CAAATGTAATAAAAGTATCAACAAAAATTGT-TAATATACCTCTATACTTTAACGT-CAAGGAGAAAAAACTATAgcggccg cTAAAATC, where the first sequence has a Mig1p-binding site deleted, while the second sequence has both a Mig1p-binding site deleted and additional Gal4p-binding sites.

Figure 8C:
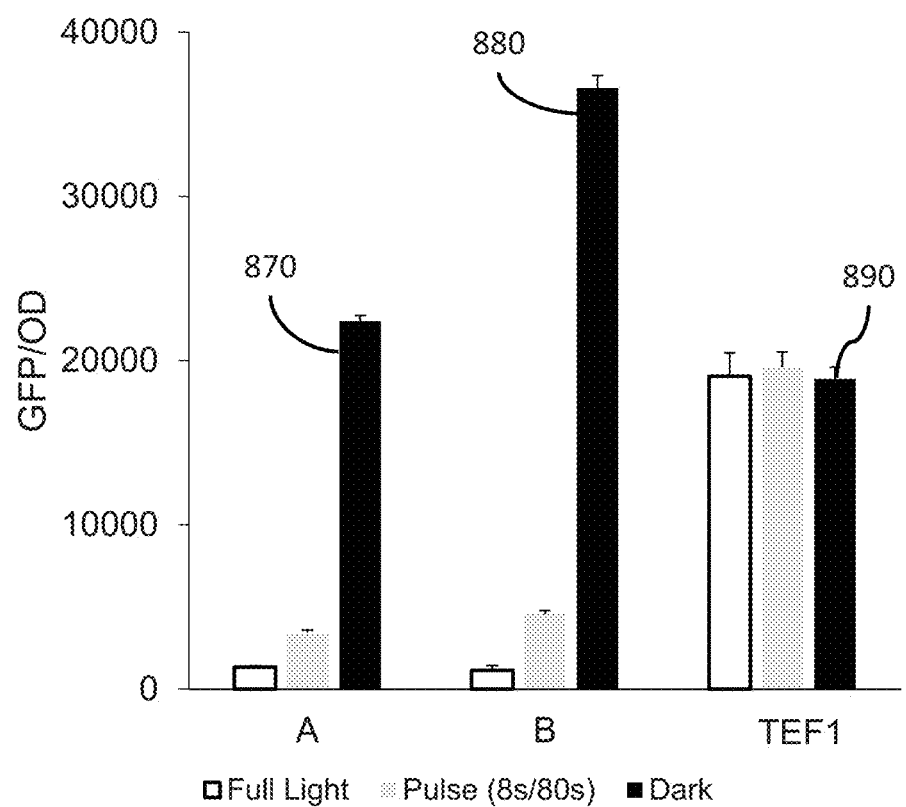

FIG. 8C compares GFP expression of YEZ31 (890) (which has $P_{TEF1}$ driving GFP expression) and OptoINVRT circuits using $P_{PGK1}$ for driving GAL4 expression, a GAL80 fused to a degron domain (in this example, an ODC mutant tag) and a $P_{GAL1}$ with a Mig1p-binding site deleted (870), or a Mig1p-binding site deleted and additional Gal4p-binding sites (880). FIG. 8C illustrates differences in fold-change responses, which offer flexibility in diverse metabolic engineering applications.

Development of an OptoEXP-PDC strain

In *S. cerevisiae* glucose fermentations, ethanol formation competes directly with any product derived from pyruvate, acetaldehyde, or acetyl-CoA. Pyruvate decarboxylation, catalyzed by three pyruvate decarboxylases (PDC1, PDC5, and PDC6), divert most of the pyruvate towards ethanol formation. However, triple deletion of these genes renders yeast unable to grow on glucose due to their essential role in the recycling of NAD$^+$ for glycolysis. The OptoEXP circuit can be used to build a metabolic valve to regulate PDC1 expression. This valve can be "opened" with light to enable a robust cell growth phase by normal fermentation and ethanol production, but then "closed" in the dark to reduce the competition of ethanol with other pyruvate-derived products during the production phase.

Strain Y200 contains a triple gene-deletion of pdc1-Δ, pdc5-Δ, and pdc6-Δ, as well as a 2μ-URA3 plasmid pJLA121PDC$^{10202}$ with $P_{TEF1}$-PDC1-$T_{ACT1}$. Y200 was transformed with linearized EZ_L165 to insert a cassette composed of $P_{TEF1}$-VP16-EL222-$T_{CYC1}$ and $P_{C120}$-PDC1-$T_{ADH1}$ into its HIS3 locus, resulting in strain YEZ50 (Supplementary Tables 1 and 2). As a control, Y200 was also transformed with linearized EZ_L158, which does not contain PDC1. Control strain YEZ50C was then produced by counter-selecting on 5-FOA (later described). This control strain lacked the PDC1 to survive on glucose in the testing. YEZ50 was then transformed with EZ_L143, which inserts multiple copies of $P_{C120}$-PDC1-$T_{ADH1}$ into 6-integration sites of the yeast genome. The resulting strain, YEZ61 is able to grow on glycerol/ethanol plates (YPGE). Colonies able to grow on YPD plates containing 800 μg/mL of Zeocin were replica plated on plates containing SC-his+3% Glycerol+2% Ethanol twice. The resulting plates were then replica plated on SC-his+3% Glycerol+2% Ethanol+5FOA, and then finally back onto plates containing SC-his+3% Glycerol+2% Ethanol. This treatment efficiently counter-selects against the URA3 marker in pJLA121-PDC1$^{0202}$plasmid, and thus the $P_{TEF1}$-PDC1 construct. From this plate YEZ61-23 was isolated, YEZ61-23 being a strain that can grow on SC-his+2% glucose plates only when exposed to blue light, which is consistent with having PDC1 expression controlled by $P_{020}$, and EL222. As a control, Y200 (which lacks EL222) was also transformed directly with EZ_L143 to produce YEZ61C. This control strain has multiple copies of $P_{C120}$-PDC1, but lacks the EL222-VP16 required to transcribe them in the presence of blue light.

Light Dependent-Growth of an OptoEXP-PDC Strain

Figure 9A:
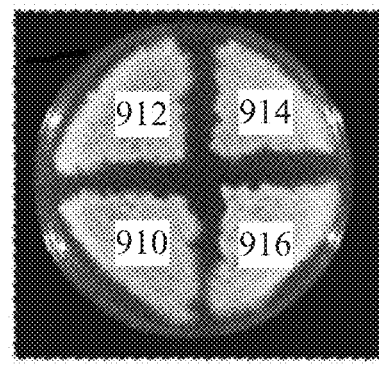
FIG. 9A depicts a replica plate of yeast strains on glycerol plates.
Figure 9B:
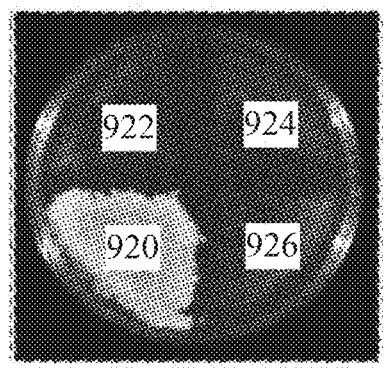
FIG. 9B depicts a replica plate of yeast strains on glucose plates grown in the darkness.
Figure 9C:
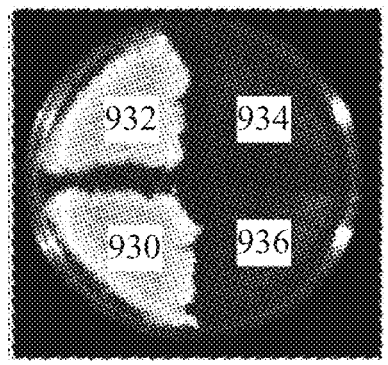
FIG. 9C depicts a replica plate of yeast strains on glucose plates grown in the light.

This is illustrated in FIGS. 9A, 9B, and 9C. Cells from the wild-type strain BY4741 (910, 920, 930), YEZ61-23 (912, 922, 932), YEZ61C (914, 924, 934), and YEZ50C (916, 926, 936) were streaked onto one YPGE plate and grown into patches. This plate was then replica plated onto one YPGE plate (FIG. 9A) and two YPD plates. One of the YPD plates was covered in tin foil (FIG. 9B) and the other exposed to constant blue light (FIG. 9C), while the YPGE was left at ambient lighting (FIG. 9A). Replica plating was done such that the YPD plate meant to be covered in tin foil was replicated first, then the YPD plate meant to be exposed to constant blue light, and the YPGE plate last. All plates were incubated at 30° C. for 48 h. FIG. 9A indicates that all strains can grow in the presence of glycerol, but FIG. 9B indicates that only the wild-type strain can grow in glucose without light. As is seen by comparing FIGS. 9B and 9C, strain YEZ61-23 (912, 922, 932) is only able to grow on glucose plates in the presence of light.

These observations are consistent with the expected loss of growth on glucose of yeast lacking PDC enzymes; indeed, no growth was observed in either triple PDC knockout or dark-incubated YEZ61 cells. In contrast, light stimulation rescued growth of only the YEZ61 strain, consistent with light-stimulated PDC1 expression mediated by the OptoEXP system.

Figure 10:
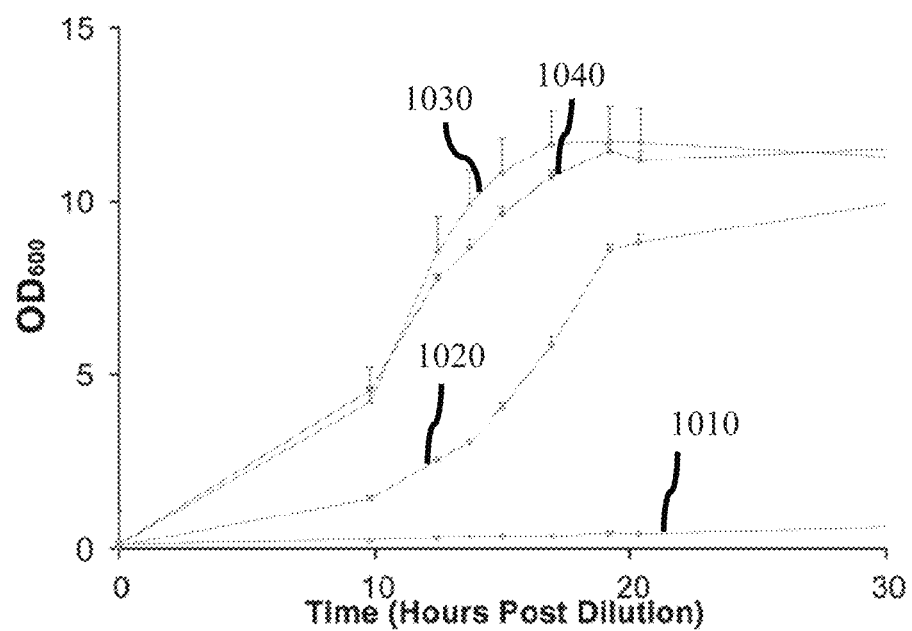
FIG. 10 is a graph of growth curves of strains with light-dependent growth, utilizing an embodiment of OptoEXP controlling PDC1.

Light-dependent growth of YEZ61 can also be observed in glucose-containing liquid medium, where growth rates were quantified under different light stimuli. As shown in FIG. 10, specific growth rate is close to zero in complete darkness (1010), where the duty cycle is 0 s/80 s. This increases with increasing light dose. Shown is a 12.5% duty cycle (1020) (10 s/80 s), and full light (1030) (80 s/80 s). With full light, the specific growth rate is approximately equal to that of the wild type strain (BY4741) (1040).

Figure 19:
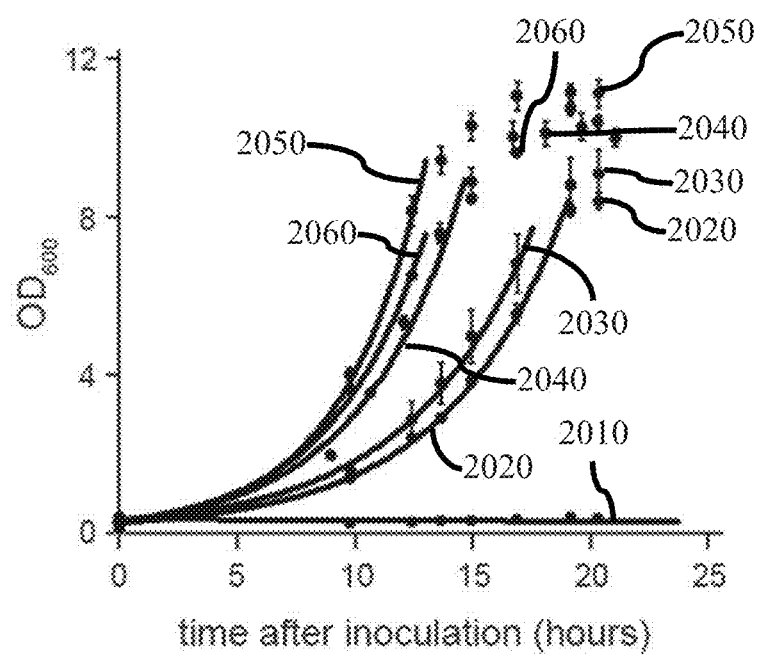
FIG. 19 is a graph of growth curves of a strain with PDC1 under OptoEXP under different duty cycles of light.

This strain was further tested by performing growth curve experiments using different light duty cycles, the results of which are shown in FIG. 19. Single colonies of YEZ61 and BY4741 were used to inoculate liquid SC-his+2% glucose medium. The cells were grown for 24 h on a roller drum at 200 rpm and 30° C. 40 cm under blue light from a HQRP New Square 12" LED Grow Light System 225 Blue LED 14 W. Subsequently, the $OD_{600}$ was measured with a spectrophotometer, and the cells were then diluted to 0.1 $OD_{600}$ in fresh SC-his 2% glucose media in three 1 mL-replicates in four 24-well plates (Celltreat® non-treated sterile flat bottom plates). The plates were incubated at 30° C. and 200 rpm for different amounts of time. Four plates were centered 40 cm under an HQRP blue light panel. The wild-type strain (2060) and one of the plates (2050) were exposed to full blue light. The other three plates were exposed to 10 s ON/70 s OFF of blue light (2020), 20 s ON/70 s OFF of blue light (2030), and 40 s ON/70 s OFF of blue light (2040). The fourth plate was wrapped in aluminum foil to incubate cells in the absence of light (2010). OD readings were taken using a TECAN plate reader at 0 h, 10 h, 12.5 h, 13.5 h, 15 h, 17 h, 19 h, 20.5 h, and 31.75 h.

Figure 11:
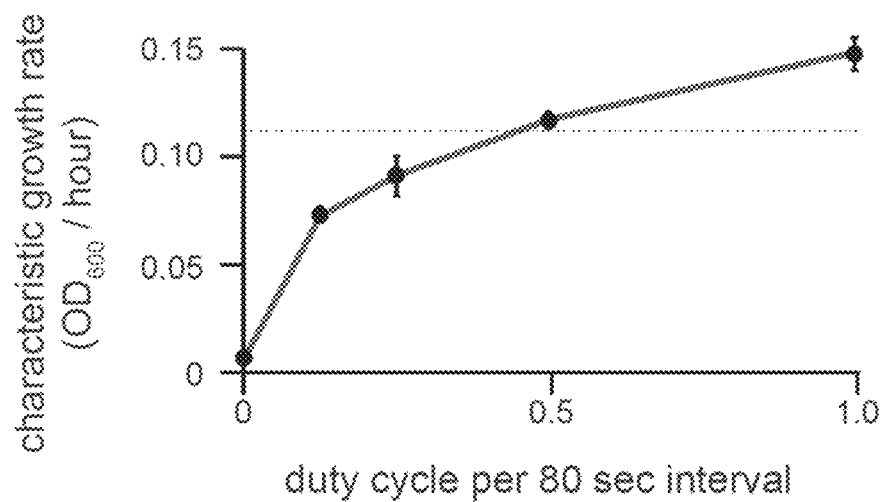
FIG. 11 is a graph of the correlation between light duty cycle and yeast maximum growth rate.

As also seen in FIG. 11, the growth rate can be controlled by varying the length of light and dark cycles. Significant growth is achieved even at relatively low light doses; applying light on a 50% duty cycle led to growth at over 100% of the wild-type rate, while a 12.5% duty cycle induced growth at 68% of the wild-type rate. This suggests that light-regulated growth may work even at the high cell densities relevant for metabolic engineering applications.

The light requirements may be lowered further by increasing the copies of $P_{C120}$-PDC1 integrated into the strain.

Generation of Chemical Production Strains

In metabolic engineering, the biosynthetic pathway for a compound of interest often competes with other pathways that cannot be deleted because they are essential for cell growth. A common case in *S. cerevisiae* is ethanol formation during fermentation, which competes directly with any product derived from pyruvate, acetaldehyde, or acetyl-CoA. In the case of pyruvate, the three isoenzymes of pyruvate decarboxylase in yeast, encoded by PDC1, PDC5, and PDC6, divert significant amounts of this key metabolite towards ethanol formation. Triple deletion of these genes results in a strain that is unable to grow on glucose either by fermentation because the product of pyruvate decarboxylase (PDC), acetaldehyde, is the electron acceptor that restores most of the $NAD^+$ for glycolysis; nor is it able to grow by respiration, because of glucose-mediated repression.

Figure 12:
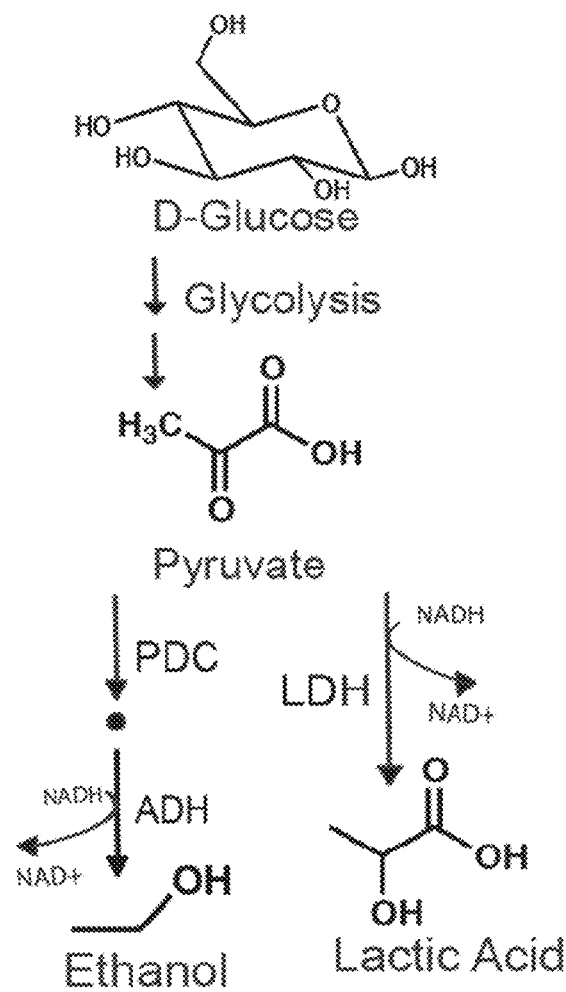
FIG. 12 depicts lactate and ethanol metabolic pathways of yeast.

OptoEXP and OptoINVRT can be used to control the growth and production phases of fermentations, shifting the yeast metabolism from ethanol to an alternative fermentation product. Arguably the simplest alternative to ethanol is lactate, which—as shown in FIG. 12—is produced by the transfer of electrons from NADH to pyruvate, a reaction catalyzed by lactate dehydrogenase (LDH). Lactate is a valuable product used in the food, drug, and cosmetic industries, as well as to produce polylactate, a biodegradable bioplastic. Its production competes directly with ethanol formation, as it is the product of pyruvate reduction, catalyzed by lactate dehydrogenase (LDH). The disclosed platform can simultaneously control PDC1 expression using OptoEXP, and LDH expression using OptoINVRT to switch cells between ethanol fermentation under blue light to lactate fermentation in the dark.

To develop photo-dependent lactic acid producing strains, linearized (with PmeI) EZ_L259, EZ_L260, and EZ_L266 (OptoINVRT1, OptoINVRT2, and OptoINVRT3 respectively) were transformed into Y202 yielding YEZ115, YEZ116, and YEZ117, respectively. In addition, multiple copies of a gene cassette (EZ_L235, Supplementary Table 1) containing $P_{C120}$ driving PDC1 and $P_{GAL1}$ driving the Lactic Acid Dehydrogenase (LDH) from *Pelodiscus sinensis* (Kindly provided by Dr. Lee from the Samsung research center) were integrated into δ-sites, producing YEZ144 (OptoINVRT1), YEZ145 (OptoINVRT2), and YEZ146 (OptoINVRT3) (Supplementary Table 2). These strains express PDC1 and repress LDH in the light, and have the opposite effect in the dark.

Figure 16:
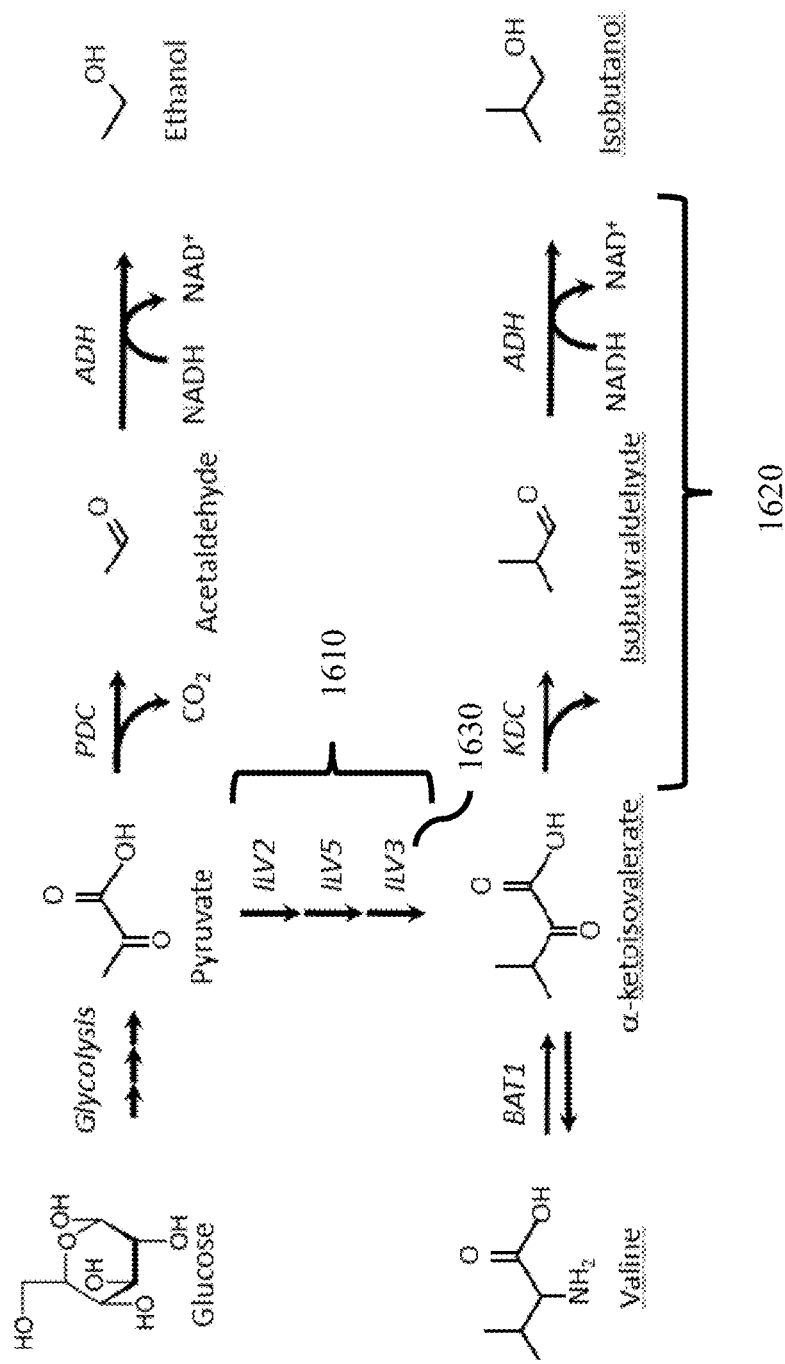
FIG. 16 depicts ethanol, isobutanol, and valine metabolic pathways of yeast.

OptoEXP and OptoINVRT can also be used to control the growth and production phases of fermentations for compounds other than lactic acid. Isobutanol is significantly more toxic than lactic acid, and as shown in FIGS. 2 and 16, has a longer biosynthetic pathway, which can be segmented in upstream (1610) and downstream (1620) pathways. The upstream pathway (1610) consists of the three first enzymes of branched-chain amino acid biosynthesis, which are contained in mitochondria: acetolactate synthase (encoded by ILV2), ketol-acid reductoisomerase (encoded by ILV5), and dihydroxyacid dehydratase (encoded by ILV3). The downstream pathway (1620) is the Ehrlich amino acid degradation pathway, which consists of two cytosolic enzymes: α-ketoacid decarboxylase (KDCs encoded by PDCs, but also ARO10, which does not act on pyruvate), and alcohol dehydrogenase (encoded by ADHs).

OptoEXP and OptoINVRT circuits can be applied to optogenetically control isobutanol production in yeast. Isobutanol is an advanced biofuel, with a much higher toxicity than lactate. One approach is to optogenetically control only the first enzyme in the isobutanol pathway, acetolactate synthase (encoded by ILV2), leaving subsequent enzymes constitutively expressed, which would enable light-control over pathway flux without accumulation of potentially undesirable intermediates.

To develop these photo-dependent isobutanol producing strains, the three OptoINVRT circuits were integrated into the HIS3 locus of Y202, as well as multiple copies of a cassette containing $P_{GAL1}$-ILV2 and $P_{C120}$-PDC1 into delta-integration sites, resulting in strains YEZ131, YEZ149, and YEZ133. Each strain was then transformed with EZ_L310 (Supplementary Table 1), a 2µ plasmid containing a complete mitochondrial isobutanol biosynthetic pathway, in which the downstream enzymes (1620) are targeted to mitochondria using the CoxIVp mitochondrial localization signal. All genes in this plasmid were expressed with strong constitutive promoters, except for ILV2, which was expressed with $P_{GAL1}$, which is under the control of OptoINVRT circuits. These transformations resulted in strains YEZ159, YEZ156, and, HPY6, for OptoINVRT1, OptoINVRT2, and OptoINVRT3, respectively.

Screens for High Lactic Acid- and Isobutanol-Producing Strains

Testing was done to determine if YEZ144, YEZ145, or YEZ146 could undergo a light-dependent metabolic shift from ethanol to lactate, and if YEZ159, YEZ156, and, HPY6 could undergo a light-dependent metabolic shift from ethanol to isobutanol.

Twelve colonies from each transformation plate (grown in glucose and under blue light) were screened for lactic acid or isobutanol production. Each colony was used to inoculate 1 mL of SC-his+2% media (for lactic acid producing strains) or SC-ura+2% glucose media (for isobutanol producing strains) in 24 well plates and grown overnight at 30 C, 200 RPM, and blue light. The next morning, each culture was diluted to 0.1 $OD_{600}$ (and 0.15 $OD_{600}$ for isobutanol producing strains) in fresh media, and grown for 16 hours (for lactic acid production) or 18 hours (for isobutanol production), again at 30 C, 200 RPM, and blue light. After these incubation periods, the cultures reached $OD_{600}$ values of 5 (for lactic acid-producing strains) and 5 and 8 (for isobutanol-producing strains); at which point they were moved into the dark for 6 hours for lactic acid producing strains and 3 hours for isobutanol producing strains. The cultures were then spun down at 1000 rpm for 5 minutes, re-suspended in fresh media, and the plates sealed with Nunc Sealing Tape (Thermo Scientific) to begin the fermentations. The plates were incubated in the dark at 30 C and shaken at 200 RPM for 48 hours during fermentation. Subsequently, the cultures were centrifuged at 1000 rpm for 10 minutes, and supernatants collected for HPLC analysis.

Figure 14:
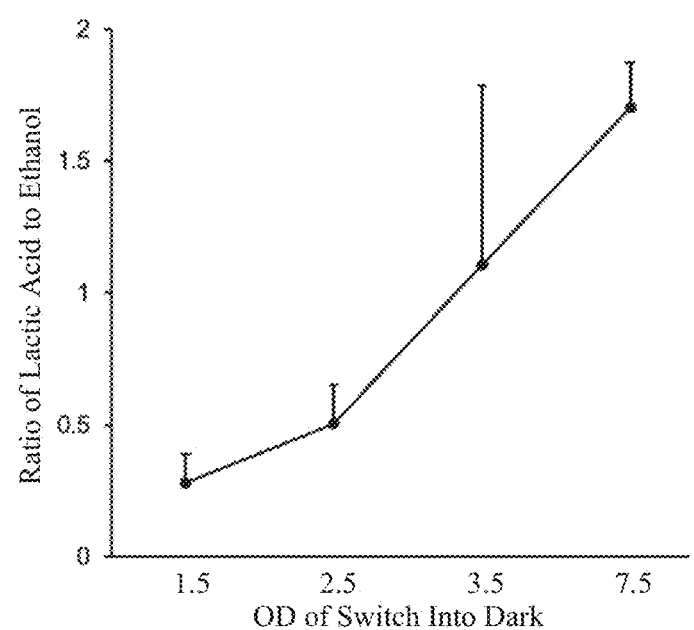
FIG. 14 is a graph of the ratio of lactic acid to ethanol production for an OptoINVRT1 embodiment moved into darkness at different ODs.
Figure 15:
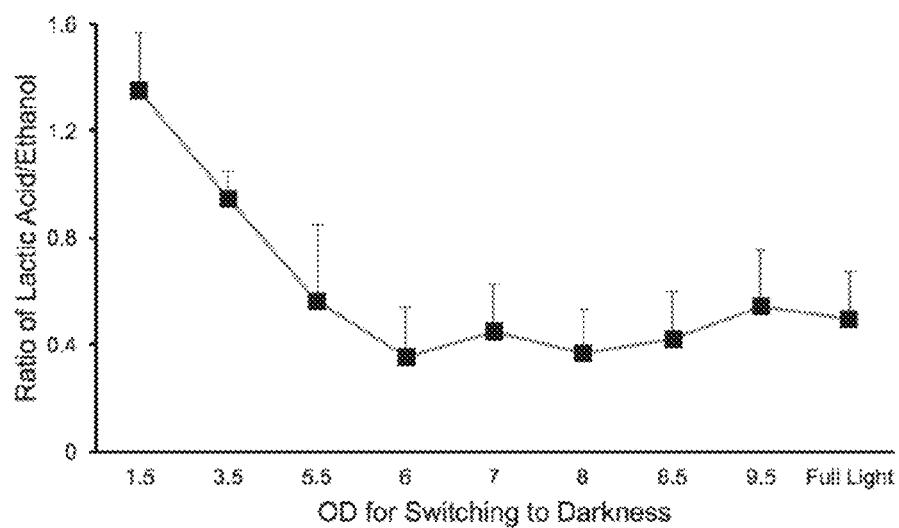
FIG. 15 is a graph of the ratio of lactic acid to ethanol production for an OptoINVRT2 embodiment moved into darkness at different ODs.

As shown in FIGS. 13A, 13C, and 13E, YEZ144 (FIG. 13A), YEZ145 (FIG. 13C), and YEZ146 (FIG. 13E) all experienced a metabolic shift when transferred from light to dark. The three OptoINVRT circuits produce different lactate titers (FIGS. 13A, 13C, and 13E) as well as lactate to ethanol ratios (FIGS. 13B, 13D, and 13F). In addition, the optical density at which the cultures are switched to the dark significantly influence lactate titers and ratios (see FIG. 14). There was an optimal OD at which cells were moved to the dark to maximize lactate production. In the case of YEZ144, as shown in FIG. 13A, the maximum shift from ethanol to lactate production (measured by the lactate/ethanol ratio) occurs when cells are moved to the dark at an OD of 7.0; this OD also corresponds to the maximum lactate titer achieved with this circuit (4.2±0.2 g/L). In YEZ145, the maximum shift (lactate to ethanol ratio) and maximum lactate titer (5.4±0.9 g/L) are reached at substantially lower ODs (1.5-3.5) (see FIGS. 13C, 13D, 15). With OptoINVRT1, switching at higher cell densities favor lactate production, whereas with OptoINVRT2 and OptoINVRT3 more lactate is produced when cells are switched at lower cell densities. In most cases, switching to the dark at any cell density results in higher lactate production than if cells are kept in the light throughout the fermentation. The exception is OptoINVRT2, where switching at OD600 values of 5.5 or higher results in the same amount of lactate produced as with cells kept in full light. This is likely due to leaky expression of GAL4 from the stronger $P_{PGK1}$, which is consistent with OptoINVRT2 producing overall the highest lactate titers.

For isobutanol producing strains, colonies from YEZ159, containing OptoINVRT1, produced the highest isobutanol titers from 4% glucose. For cells moved from the light to dark at an $OD_{600}$ of 8, colonies from YEZ159, containing OptoINVRT1, were most effective at producing isobutanol from 4% glucose, compared to colonies containing OptoINVRT2 or OptoINVRT3. The same trend continued for cells moved from the light to dark at an $OD_{600}$ of 5, where colonies containing OptoINVRT1 were more effective at producing isobutanol than colonies containing OptoINVRT2 or OptoINVRT3.

To further enhance isobutanol production, the mitochondrial branched chain amino acid aminotransferase, BAT1, which competes for α-ketoisovalerate precursor, was deleted from YEZ131, and the resulting strain (YEZ158) was transformed with plasmid EZ_L310 to produce strain YEZ167 (Supplementary Tables 1 and 2). After screening seven colonies of YEZ167, as above, YEZ167-4 was identified as the highest isobutanol producer.

Figure 17A:
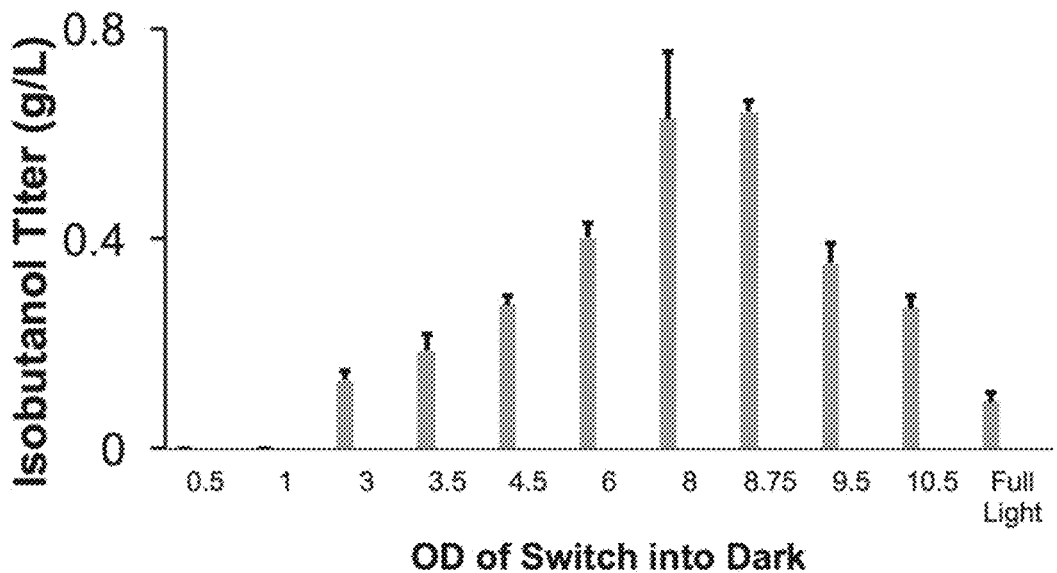
FIG. 17A is a graph of isobutanol production for a strain containing ethanol pathway under OptoEXP (PDC1), and isobutanol pathways under OptoINVRT1 moved into darkness at different ODs.
Figure 17B:
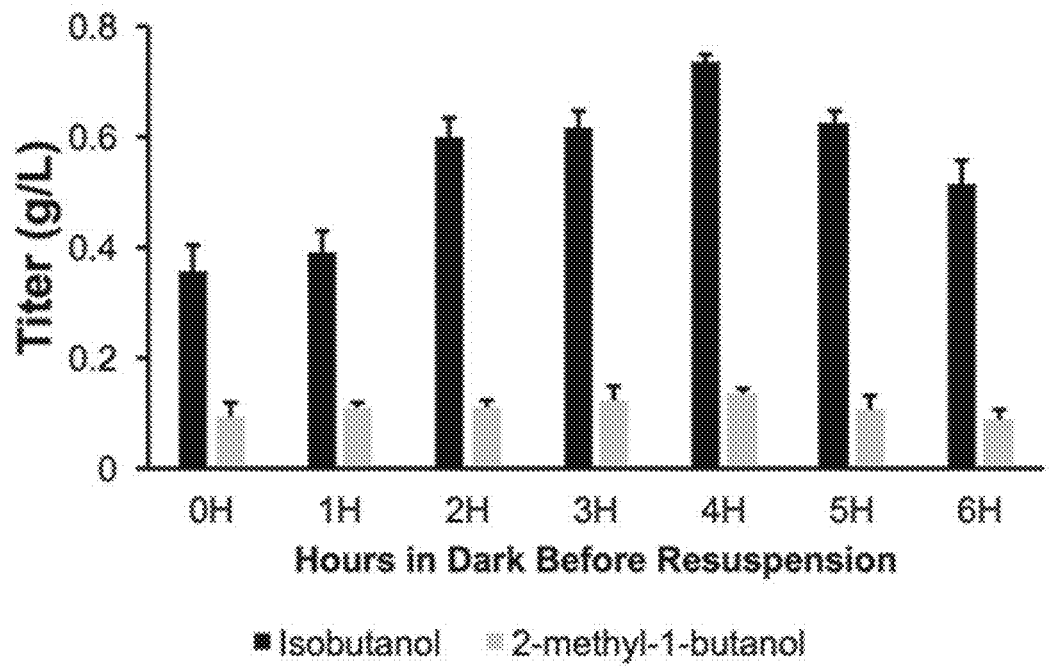
FIG. 17B is a graph of isobutanol and 2-methyl-1-butanol production for a strain containing ethanol pathway under OptoEXP (PDC1), and isobutanol pathways under OptoINVRT1 held in dark for different hours prior to fermentation.

In addition to varying the OD at which cells were moved from light to dark, the incubation time before resuspending cells in fresh medium to start the fermentation was also varied. At the optimal values for this example system—$OD_{600}$ of transfer to dark of 8.0-8.8 (see FIG. 17A), and incubation in the dark of 4 hours (see FIG. 17B)—strain YEZ167-4 produces 735±15 mg/L from 2% glucose, over 48 hours, representing a yield of 34.2±0.7 mg isobutanol/g glucose.

Figure 18:
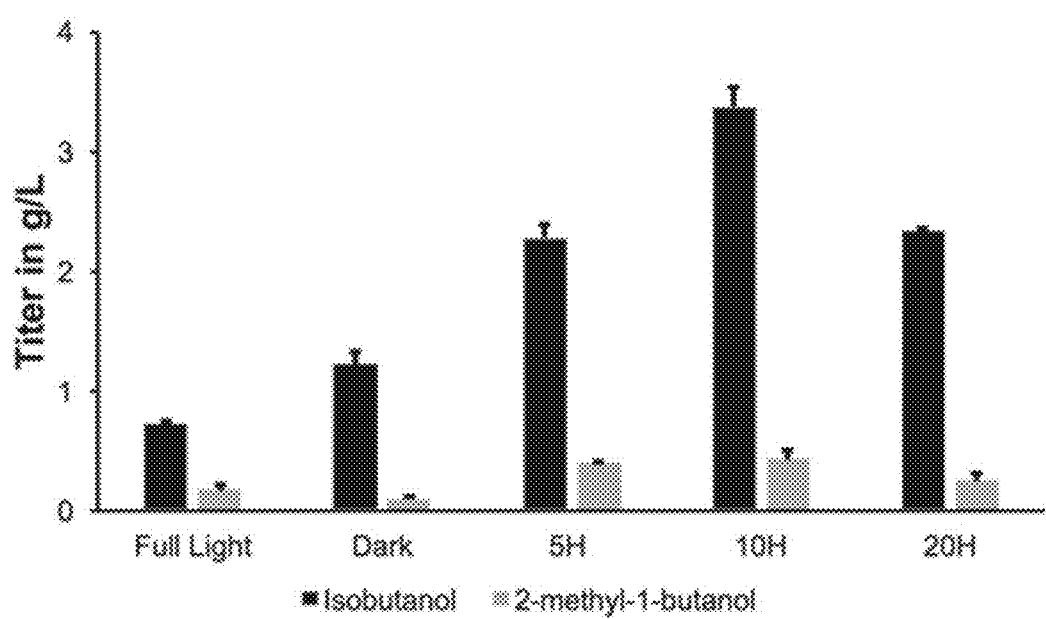
FIG. 18 is a graph of isobutanol and 2-methyl-1-butanol production from a strain containing the ethanol pathway (PDC1) under the control of OptoEXP, and the isobutanol pathway under the control of OptoINVRT1, exposed to light schedules consisting of 30 minutes of light exposure at a duty cycle of 15 s on/65 s off.

To boost isobutanol titers, the glucose concentration and time of fermentation was increased. After 72 hours of fermenting in the dark with 15% glucose, YEZ167-4 produces 1.22±0.11 g/L of isobutanol. However, cells were unable to consume all the glucose in the medium, suggesting cells under these conditions can become limited by Pdc1p to a point where their metabolism arrests due to $NAD^+$ depletion. Periodic pulses of light during the fermentation can transiently induce PDC1 expression, thus increasing $NAD^+$ pools, thereby restoring cellular metabolism, glucose consumption, and isobutanol production. Different light schedules were tested, consisting of 30 minutes of light at exposure at a duty cycle of 15 s/65 s, every 5 h, 10 h, or 20 h, repeated throughout the 72 hour long fermentation. Indeed, as shown in FIG. 18, isobutanol production tripled to 3.37±0.17 g/L when cells were exposed to this light regimen every 10 hours. The mitochondrial isobutanol pathway can also increase the production of 2-methyl-1-butanol (see Avalos et al. 2013), another desirable advanced biofuel. Under these same conditions, YEZ167-4 produced 433±69 mg/L of 2-methyl-1-butanol (FIG. 18).

Fermentation Optimization

Cell Density Optimization.

The highest producing strains identified above were used to optimize the pre-growth parameters of fermentation for lactic acid or isobutanol production. For each strain, an overnight culture was grown in blue light, 30° C. and shaking at 200RPM, in 2% glucose-containing SC media (SC-his+2% glucose for lactic acid producing strains and SC-ura+2% glucose for isobutanol producing strains). To optimize the cell density at which cultures are switched from light to dark, the overnight cultures were diluted into 1 mL of the SC dropout medium to different $OD_{600}$ values, ranging from 0.04 to 0.32. The lactic acid-producing strains were then grown for 16 hours under 15 s on/65 s off blue light. The isobutanol-producing strains were grown for 18 hours under 15 s on/65 s off blue light. In one early test, the cultures were then incubated in the dark for 6 hours for lactic acid-producing strains and 3 hours for isobutanol-producing strains, although later it was determined that 4 hours produced better results for isobutanol production. After this dark incubation period, the cultures were centrifuged at 1000 rpm for 5 minutes and suspended in fresh SC dropout media containing glucose at 26.5% (for lactic-acid producing strains) or 21.5% (for isobutanol-producing strains). The plates were sealed with Nunc Sealing Tape, and incubated in the dark for fermentation at 30° C., 200RPM. Control cultures were grown under 15 s on/65 s off blue light during the growth phase (the dark incubation period), and during the fermentation. Cultures producing lactic acid were harvested after 48 hours, while samples of cultures producing isobutanol were taken after 24, 48, and 72 hours. Cultures were centrifuged at 1000 rpm for 10 minutes, and supernatants analyzed with HPLC.

Dark Incubation Period Optimization.

To optimize the dark incubation period before fermentation, the best isobutanol-producing strain, YEZ167-4, was grown overnight under blue light in SC-ura, 2% glucose. The overnight culture was then diluted into seven different plates in quadruplicate samples in fresh media to a starting $OD_{600}$ of 0.1. The cultures were then grown to an $OD_{600}$ of 8.5 (which was found to be the optimal $OD_{600}$ in a previous experiment). At that point, the plates were tin foiled to ensure complete darkness; after every hour, one of the plates was centrifuged, and the cells suspended in fresh SC-ura medium with 20.8 g/L glucose media for 48 hour fermentations in the dark.

Fermentation Light Pulse Optimization.

To alleviate any Pdc1p limitation, periodic pulses of light during the fermentation can be used to induce transient expression of PDC1, which restores some metabolic balance to allow cells to consume all the glucose in the medium and produce more isobutanol. A single colony of the best isobutanol producing strain, YEZ167-4, was used to inoculate 5 mL of SC-URA+4% glucose media and grown overnight under light. The next morning, the culture was diluted in 1 mL of fresh media to an $OD_{600}$ of 0.2 (in quadruplicates) and grown under full light for 20 hours to an $OD_{600}$ of 9.5. Subsequently, in this early test, the cultures were incubated for 3 hours in the dark, before it was determined that 4 hours yielded better results. To start the fermentations, the cultures were centrifuged again, and suspended in fresh SC-URA+ 15% glucose (precisely 157.0 g/L glucose, as measured with HPLC) media, and kept in the dark. During the fermentation, the cultures were pulsed every 5, 10, or 20 hours for 30 minutes, at a duty cycle of 15 s On/65 s Off. As controls, some plates were always kept in the dark or in full light. Fermentations lasted for 80 hours, after which, the cultures were centrifuged, and the supernatants analyzed with HPLC.

As shown in FIG. 18, cells exposed to 30 minutes of light every 10 hours tripled their isobutanol output to 3.371±0.167 g/L. While the only parameter optimized in this example is the time between pulses during the fermentation, many other parameters exist that could also be optimized, including but not limited to duty cycle, light intensity, pulse length, and parameter variation during fermentation.

Further, this example of high isobutanol yields and titers were achieved using a strain with a suboptimal genetic background. In addition to the mitochondrial isobutanol biosynthetic pathway and optogenetic controls, the only genetic improvement of YEZ167-4 is the deletion of bat1-Δ, which has been shown to enhance isobutanol production. However, there are several other genetic modifications that would likely further increase isobutanol production, such as overexpression of Mitochondrial malic enzyme (MAE1, Matsuda *Microbial Cell Factories* 2013), or Mitochondrial pyruvate carriers (MPCs, Park *Applied Genetics and Molecular Biotechnology* 2016); or deletion of acetyl-CoA synthesis (LPD1, Park *Applied Genetics and Molecular Biotechnology* 2016) or aldehyde dehydrogenase (ALD6, Park *Applied Genetics and Molecular Biotechnology* 2016).

In addition, the isobutanol pathway used in this example (See FIG. 16) uses an NADPH-dependent KARI (ILV3) (1630), which can recover only half of the NAD+ consumed in glycolysis (via ADH activity). However, other approaches for improving isobutanol production are envisioned, including but not limited to modifying the isobutanol pathway to include an NADH-dependent KARI, or utilizing a transhydrogenase, isobutanol formation could be able to recycle all the NAD+ needed for glycolysis (Brinkmann-Chen PNAS 2013).

The mitochondrial isobutanol pathway can also significantly increase the production of isopentanol and 2-methyl-1-butanol (Avalos et. al. 2013). Thus, 2-methyl-1-butanol production was also measured. Isopentanol production is not expected due to the LEU2 auxotrophic marker of the example strains (which blocks leucine biosynthesis and thus isopentanol production). A expected, YEZ167-4 shows increased 2-methyl-1-butanol production (FIG. 18), which is also sensitive to blue light pulses during fermentation, reaching a maximum of 433.0±69.2 mg/L at 10 hour intervals of 30 minute blue light exposure, the same as the isobutanol maximum.

Scaled Fermentation and Growth of Isobutanol-Producing Strains

To test if enough blue light can penetrate high cell density fermentations in larger volumes to control engineered metabolisms, the ability of YEZ167-4 to grow to high $OD_{600}$ values was tested in a 2 L fermenter. As a control, the growth of YEZ167-4 was compared to that of YZy335, which is a strain that constitutively makes isobutanol and has all three native PDC1, PDC5, and PDC6 still intact (such that growth and isobutanol production in this strain is independent of light).

Figure 20:
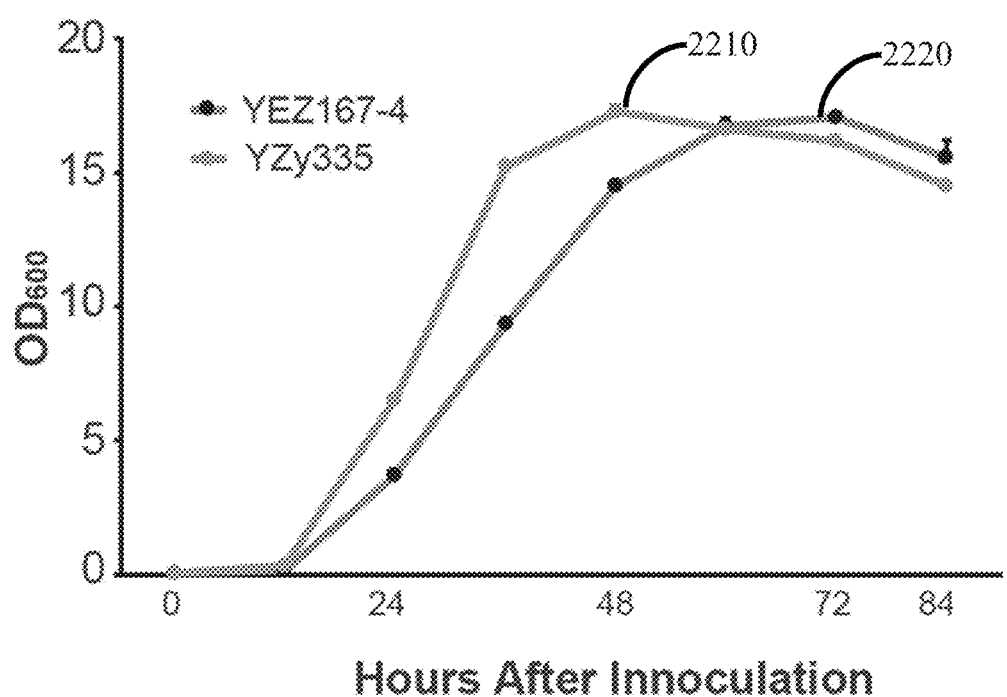
FIG. 20 is a graph illustrating the growth of a strain containing ethanol pathway under OptoEXP (PDC1), and isobutanol pathways under OptoINVRT1 (YEZ167-4), compared to a strain with wild-type control of PDC1, and constitutive isobutanol pathway (YZy335).

To test growth of YEZ167-4 in a 2 L fermenter, a single colony was used to inoculate 5 mL of SC-ura+2% glucose media under light, overnight. The next morning, the culture was diluted in SC-ura+15% glucose media to an $OD_{600}$ of 0.1 in a 2-Liter glass bioreactor surrounded by three blue light panels, placed at 1 cm from the glass wall of the reactor. The culture was also stirred using a stir bar and bubbled with air. The control strain YZy335 was grown using the same conditions. Samples were taken every 12 hours to measure the $OD_{600}$ of the cell cultures. As shown in FIG. 20, YEZ167-4 (2220) was able to reach the same optical density (OD600=17) as the PDC+ control strain, YZy335 (2210), with a small delay most likely due to the weaker $P_{C120}$ promoter driving PDC1 expression in YEZ167-4 relative to $P_{PDC1}$ in the wild-type.

Fed-Batch Fermentation

Figure 26:
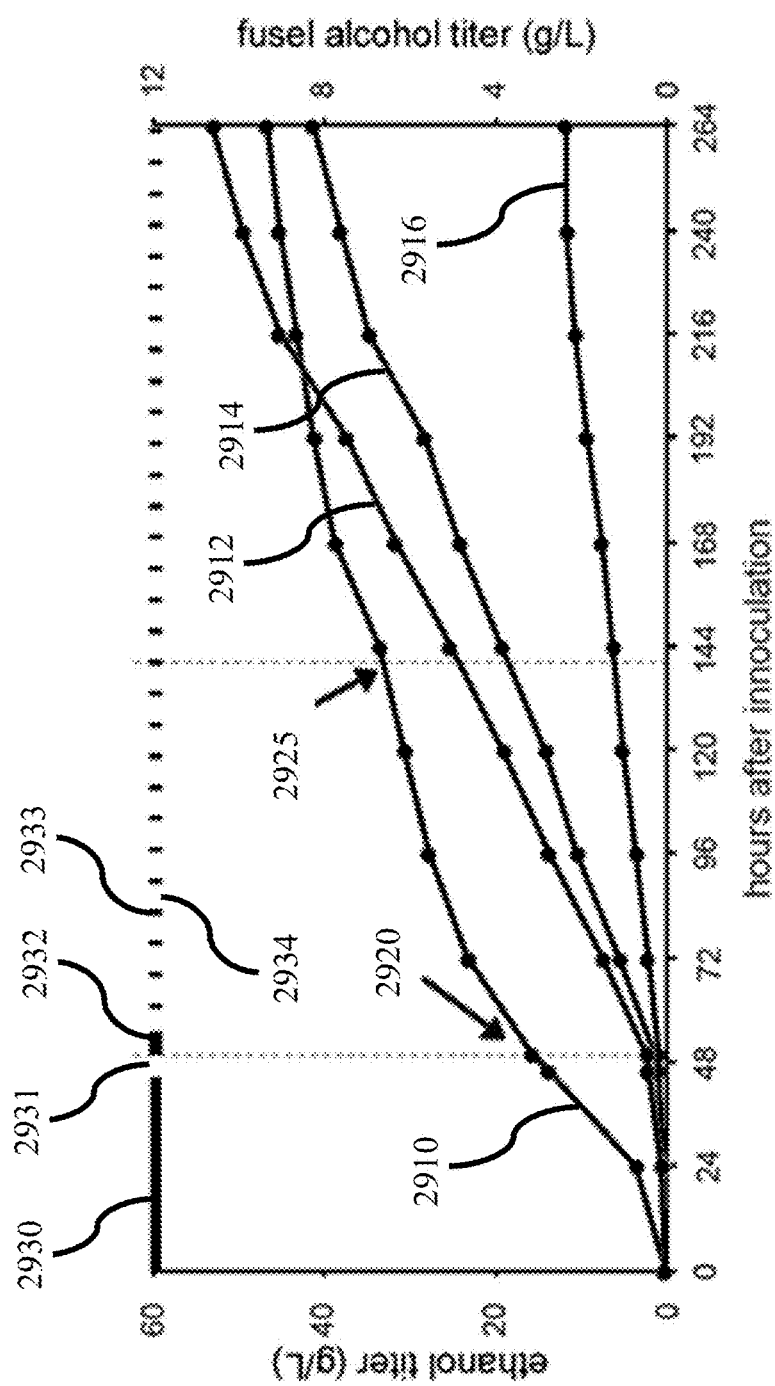
FIG. 26 is time course fermentation data for a fed-batch fermentation for isobutanol production (YEZ167-4)

Isobutanol production under microaerobic conditions in a 0.5 L fermenter was then tested using the Sixfors INFORS AG CH-4103 based on a previously described set up (The Use of Chemostats in Microbial Systems Biology, Gresham JOVE). However, dissolved oxygen probe and air pumps were not used. The pH was set to 5.5 with 10M KOH fed in to raise the pH when needed through the base pump. The 500 mL fermenter was autoclaved with ddH2O and exchanged the ddH2O with 250 mL of SC-ura+10% glucose media using the air pump manually. A single colony of YEZ167-4 was used to inoculate 5 mL of SC-ura+2% glucose media. In FIG. 26, the black bar across the top of the graph is used to illustrate when in this experiment the light was on (2930, 2932, 2933), and those times where no black bar is present indicates the light was off (2931, 2934). Here, YEZ167-4 cells were grown in batch mode with light (2930) to an $OD_{600}=8.2$, at which point, the light was turned off for 4 hours (2931). Subsequently, a glucose feed was started (2920) and the light was turned back on for 4 hours (2932) before exposing the fermenter to a light schedule of 0.75 hours on (2933)/7.25 hours off (2934), for 216 hours. At 140 hours after inoculation, the glucose feed was stopped (2925). FIG. 26 depicts the measured titers of ethanol (2910), total fusel alcohol (2912), isobutanol (2914) and 2-methyl-1-butanol (2916). Under these conditions, 8.2 g/L of isobutanol was produced along with 2.3 g/L of 2-methyl-1-butanol. In addition, the average isobutanol yield in the last two days of the fermentation was 79±9 mg of isobutanol per gram of glucose, which is approximately 20% of the theoretical maximum.

Small Molecule Analysis

The concentrations of glucose, lactic acid, ethanol and isobutanol were quantified with high-performance liquid chromatography (HPLC), using an Agilent 1260 Infinity instrument (Agilent Technologies, Santa Clara, CA, USA). Samples were centrifuged to remove cells and other solid debris, and analyzed using an Aminex® HPX-87H ion-exchange column (Bio-Rad, Richmond, CA, USA). The column was eluted with a mobile phase of 5 mM sulfuric acid at 55° C. and a flow rate of 0.6 ml/min. Glucose, lactic acid, ethanol and isobutanol were monitored with a refractive index detector (RID). To determine their concentration, the peak areas were measured and compared to those of standard solutions for quantification.

Flow Cytometry Measurements

To confirm the plate reader results, flow cytometry was used on the OptoEXP system. To do this, CEN.PK-2C was transformed with pYZ12-B (an empty his vector), EZ_L136, and EZ_L350 to make YEZ140 (CEN.PK-2C with his auxotrophy restored), YEZ139 (CEN.PK-2C with OptoEXP driving GFP), and YEZ186 (CEN.PK-2C with his::$P_{TEF1}$_GFP_$T_{ACT1}$), respectively. These strains were grown overnight in SC-his+2% glucose media in the dark. 20 uL of these cultures was then diluted into 980 uL of fresh media in two 24-well plates. One plate was placed 0.4 m under a blue light panel and the other was tin-foiled and kept in the dark. Both plates were shaken at 200 rpm at 30° C. for 8 hours. Then, 5 uL of culture was diluted into 995 uL of phosphate-buffered saline media and used for flow cytometry. Samples were run in triplicates from three different cultures separated after the overnight stage.

GFP expression was quantified by flow cytometry using a BD LSR II flow cytometer (BD Biosciences, San Jose, CA, USA) with the excitation wavelength of 488 nm and the emission wavelength of 530 nm. Mean fluorescence values were determined from 20 000 cells. Data were analyzed with the FlowJo® Version 10 analysis software (Tree Star, Ashland, OR, USA).

SUPPLEMENTARY TABLE 1

Plasmids Utilized

| Plasmid Name | Contents | Markers (Yeast) | Description | Yeast Transformation type |
|---|---|---|---|---|
| pJLA_03_01 | $P_{PGK1}$_Multiple Cloning Sequence (MCS)_$T_{CYC1}$ | URA3 | Control Plasmid for Ura3 2μ | 2μ |
| pYZ12-B | HIS3-locus Integration Plasmid | HIS3 | His Integration | Integration into HIS3 Locus |
| pYZ23 | Delta Integration Plasmid | Delta Integration (Selected with Zeocin) | Delta Integration with Ble Resistance | Integration in to Delta transposon sites |
| pJLA121PDC1[0202] | $P_{TEF1}$_PDC1_$T_{ACT1}$ | URA3 | Constitutive TEF | 2μ |
| pJA192 | $P_{PGK1}$_ScILV3_$T_{Cyc1}$ + $P_{TEF1}$_CoxIV_LlAdhARE1_$P_{ACT1}$ + $P_{TDH3}$_ScILV2_$T_{ADH1}$ + $P_{TDH3}$_CoxIV_ScARO10_$T_{ADH1}$ + $P_{TEF1}$_ScILV5_$T_{ACT1}$, from Avalos 2013 | UR43 | Constitutive Isobutanol Mitochondrial Pathway | 2μ |
| EZ_L63 | $P_{ADH1}$_GFP_$T_{ACT1}$ | URA3 | Single Copy Adh1 Long promoter | CEN |
| EZ_L64 | $P_{CYC1}$_GFP_$T_{ADH1}$ | URA3 | Single Copy Cyc1 promoter | CEN |
| EZ_L65 | $P_{TDH3}$_GFP_$T_{ADH1}$ | URA3 | Single Copy TDH3 promoter | CEN |
| EZ_L66 | $P_{TEF1}$_GFP_$T_{ACT1}$ | URA3 | Single Copy TEF1 promoter | CEN |
| EZ_L67 | $P_{PGK1}$_GFP_$T_{CYC1}$ | URA3 | Single Copy PGK1 promoter | CEN |
| EZ_L83 | $P_{C120}$_GFP_$T_{ADH1}$ | URA3 | Single Copy C120 promoter | CEN |

SUPPLEMENTARY TABLE 1-continued

Plasmids Utilized

| Plasmid Name | Contents | Markers (Yeast) | Description | Yeast Transformation type |
|---|---|---|---|---|
| EZ_L105 | $P_{PGK1}$_VP16-EL222_$T_{CYC1}$ | HIS3 | His Integration of VP16-EL222 System | Integration into HIS3 Locus |
| EZ_L136 | $P_{TEF1}$_VP16-EL222_$T_{CYC1}$_$P_{C120}$_GFP_$T_{ADH1}$ | HIS3 | His Integration of OptoEXP | Integration into HIS3 Locus |
| EZ_L143 | $P_{C120}$_PDC1_$T_{ADH1}$ | Delta Integration (Selected with Zeocin) PDC1 | Multiple Integration of C120 driving | Integration in to Delta transposon sites |
| EZ_L158 | $P_{TEF1}$_VP16-EL222_$T_{CYC1}$ | HIS3 | His Integration of VP16-EL222 System | Integration into HIS3 Locus |
| EZ_L165 | $P_{TEF1}$_VP16-EL222_$T_{CYC1}$ + $P_{C120}$_PDC1_$T_{ADH1}$ | HIS3 | His Integration of VP16-EL222 System and Single Copy of PDC1 | Integration into HIS3 Locus |
| EZ_L259 | $P_{TEF1}$_VP16-EL222_$T_{CYC1}$ + $P_{C120}$_GAL80_$T_{ACT1}$ + $P_{GAL1}$_GFP_$T_{ADH1}$ + $P_{C120}$_GAL80_$T_{ADH1}$ + $P_{ADH1}$_GAL4_$T_{ACT1}$ | HIS3 | OptoREP1 Circuit with GFP marker | Integration into HIS3 Locus |
| EZ_L260 | $P_{TEF1}$_VP16-EL222_$T_{CYC1}$ + $P_{C120}$_GAL80_$T_{ACT1}$ + $P_{GAL1}$_GFP_$T_{ADH1}$ + $P_{C120}$_GAL80_$T_{ADH1}$ + $P_{PGK1}$_GAL4_$T_{ACT1}$ | HIS3 | OptoREP2 Circuit with GFP marker | Integration into HIS3 Locus |
| EZ_L266 | $P_{TEF1}$_VP16-EL222_$T_{CYC1}$ + $P_{C120}$_GAL80_$T_{ACT1}$ + $P_{GAL1}$_GFP_$T_{ADH1}$ + $P_{C120}$_GAL80_$T_{ACT1}$ + $P_{PGK1}$_GAL4_PSD_$T_{ADH1}$ | HIS3 | OptoREP3 Circuit with GFP marker PSD = Photo-sensitive degron | Integration into HIS3 Locus |
| EZ_L225 | $P_{GAL1}$_LDH_$T_{ADH1}$ | URA3 | S288C GAL1 promoter driving Lactate Dehydrogenase (LDH) | 2µ |
| EZ_L226 | $P_{GAL1\_CENPK}$_LDH_$T_{ADH1}$ | URA3 | CENPK2-1C GAL1 promoter driving Lactate Dehydrogenase (LDH) | 2µ |
| EZ_L235 | $P_{C120}$_PDC1_$T_{ACT1}$ + $P_{GAL1}$_LDH_$T_{ADH1}$ | Delta Integration (Selected with Zeocin) | Multiple Copies of OptoEXP-PDC1 and OptoREP-LDH | Integration in to Delta transposon sites |
| EZ_L236 | $P_{C120}$_PDC1_$T_{ACT1}$ + $P_{GAL1}$_CENPK—LDH_$T_{ADH1}$ | Delta Integration (Selected with Zeocin) | Multiple Copies of OptoEXP-PDC1 and OptoREP-LDH (CENPK2-1C Version of promoter) | Integration in to Delta transposon sites |
| EZ_L310 | $P_{PGK1}$_ScILV3_$T_{Cyc1}$ + $P_{TEF1}$_CoxIV_LlAdhARE1_$P_{ACT1}$ + $P_{GAL1}$_ScILV2_$T_{ADH1}$ + $P_{TDH3}$_CoxIV_ScARO10_$T_{ADH1}$ + $P_{TEF1}$_ScILV5_$T_{ACT1}$ | URA3 | Full Mitochondrial pathway for Isobutanol with OptoREP-ILV2 | 2µ |
| EZ_L316 | $P_{C120}$_PDC1_$T_{ADH1}$ + $P_{GAL1}$_ScILV2_$T_{ADH1}$ | Delta Integration (Selected with Zeocin) | Multiple Copies of OptoEXP-PDC1 and OptoREP-ILV2 | Integration in to Delta transposon sites |

SUPPLEMENTARY TABLE 2

Yeast Strains Utilized

| Strain Name | Genotype | Description |
|---|---|---|
| BY4741 | S288C MATa his3Δ1 leu2Δ0 met15Δ0 ura3Δ0 | Basis Strain for Experiments |

SUPPLEMENTARY TABLE 2-continued

Yeast Strains Utilized

| Strain Name | Genotype | Description |
| --- | --- | --- |
| CEN.PK2-1C | MATa his3Δ1 leu2-3_112 trp1-289 ura3-53 | Basis Strain for Experiments |
| Y200 | BY4741 pdc1Δ1 pdc5Δ1 pdc6Δ1 + pJLA121PDC1$^{0202}$ | Strain that does not produce any PDCp |
| Y202 | BY4741 pdc1Δ1 pdc5Δ1 pdc6Δ1 gal80Δ1 + pJLA121PDC1$^{0202}$ | Strain that does not produce any PDCp or Gal80p |
| YEZ24 | CEN.PK2-1C HIS3$_{cg}$::P$_{PGK1}$_VP16-EL222_T$_{CYC1}$ | EL222 Blue light expression system Integrated |
| YEZ25 | CEN.PK2-1C gal80 | Strain that does not produce Gal4p and Gal80p |
| YEZ27 | CEN.PK2-1C + EZ_L64 | Constitutively active GFP |
| YEZ28 | CEN.PK2-1C + EZ_L63 | Single Copy, P$_{CYC1}$ Constitutively active GFP |
| YEZ29 | CEN.PK2-1C + EZ_L67 | Single Copy, P$_{ADH1}$_ Constitutively active GFP |
| YEZ30 | CEN.PK2-1C + EZ_L65 | Single Copy, P$_{PGK1}$_ Constitutively active GFP |
| YEZ31 | CEN.PK2-1C + EZ_L66 | Single Copy, P$_{TDH3}$— Constitutively active GFP |
| YEZ32 | CEN.PK2-1C HIS3$_{cg}$::P$_{PGK1}$_VP16-EL222 T$_{CYC1}$ + EZ_L83 | Single Copy, P$_{TEF1}$— OptoEXP driving GFP |
| YEZ32C | CEN.PK2-1C HIS3$_{cg}$::P$_{PGK1}$_VP16-EL222_T$_{CYC1}$ + pRSII416 | OptoEXP Control |
| YEZ44 | CEN.PK2-1C gal4 gal80 | Strain that does not produce Gal4p and Gal80p |
| YEZ50 | Y202 HIS3$_{cg}$::P$_{TEF1}$_VP16-EL222_T$_{CYC1}$_P$_{C120}$_PDC1_T$_{ADH1}$ | Add PDC1 activated in blue light |
| YEZ50C | Y202 HIS3$_{cg}$::P$_{TEF1}$_VP16-EL222_T$_{CYC1}$ | Add just EL222 system, control for YEZ61 |
| YEZ61 | Y202 HIS3$_{cg}$::P$_{TEF1}$_VP16-EL222_T$_{CYC1}$_P$_{C120}$_PDC1_T$_{ADH1}$ +EZ_L143, Lost pJLA121PDC1$^{0202}$ | Add PDC1 activated in blue light and extra copies of PDC1 |
| YEZ61C | Y202 + EZ_L143, lost pJLA121PDC1$^{0202}$ | Add extra copies of PDC1, control for YEZ61 |
| YEZ100 | YEZ44 HIS3$_{cg}$::P$_{TEF1}$_VP16-EL222_T$_{CYC1}$_P$_{C120}$_GAL80_T$_{ACT1}$_P$_{GAL1}$_GFP_T$_{ADH1}$_P$_{C120}$_GAL80_T$_{ADH1}$_P$_{ADH1}$_GAL4_T$_{ACT1}$ | OptoINVRT1 in CEN.PK with Gal4 and Gal80 Knocked out |
| YEZ101 | YEZ44 HIS3$_{cg}$::P$_{TEF1}$_VP16-EL222_T$_{CYC1}$_P$_{C120}$_GAL80_T$_{ACT1}$_P$_{GAL1}$_GFP_T$_{ADH1}$_P$_{C120}$_GAL80_T$_{ADH1}$_P$_{PGK1}$_GAL4_T$_{ACT1}$ | OptoINVRT2 in CEN.PK with Gal4 and Gal80 Knocked out |
| YEZ102 | YEZ44 HIS3$_{cg}$::P$_{TEF1}$_VP16-EL222_T$_{CYC1}$_P$_{C120}$_GAL80_T$_{ACT1}$_P$_{GAL1}$_GFP_T$_{ADH1}$_P$_{C120}$_GAL80_T$_{ADH1}$_P$_{PGK1}$_GAL4_T$_{ACT1}$ | OptoINVRT3 in CEN.PK with Gal4 and Gal80 Knocked out |
| YEZ115 | Y202 HIS3$_{cg}$::P$_{TEF1}$_VP16-EL222_T$_{CYC1}$_P$_{C120}$_GAL80_T$_{ACT1}$_P$_{GAL1}$_GFP_T$_{ADH1}$_P$_{C120}$_GAL80_T$_{ADH1}$_P$_{ADH1}$_GAL4_T$_{ACT1}$ + pJLA121PDC1$^{0202}$ | OptoINVRT1 in a PDC1, PDC5, PDC6, GAL80 Knockout. Also has URA3 plasmid with constitutive PDC1, so still can grow on glucose. |
| YEZ116 | Y202 HIS3$_{cg}$::P$_{TEF1}$_VP16-EL222_T$_{CYC1}$_P$_{C120}$_GAL80_T$_{ACT1}$_P$_{GAL1}$_GFP_T$_{ADH1}$_P$_{C120}$_GAL80__TADH1_P$_{PGK1}$_GAL4_T$_{ACT1}$ + pJLA121PDC1$^{0202}$ | OptoINVRT2 in a PDC1, PDC5, PDC6, GAL80 Knockout. Also has URA3 plasmid with constitutive PDC1, so still can grow on glucose. |

SUPPLEMENTARY TABLE 2-continued

Yeast Strains Utilized

| Strain Name | Genotype | Description |
|---|---|---|
| YEZ117 | Y202 HIS3$_{cg}$::P$_{TEF1}$_VP16-EL222_T$_{CYC1}$_P$_{C120}$_GAL80_T$_{ACT1}$_P$_{GAL1}$_GFP_T$_{ADH1}$_P$_{C120}$_GAL80_T$_{ADH1}$_P$_{PGK1}$_GAL4_PSD_T$_{ACT1}$ + pJLA121PDC1$^{0202}$ | OptoINVRT3 in a PDC1, PDC5, PDC6, GAL80 Knockout. Also has URA3 plasmid with constitutive PDC1, so still can grow on glucose. |
| YEZ131 | YEZ115 + EZ_L316, Lost Plasmid | OptoINVRT1 in a PDC1, PDC5, PDC6, GAL80 a Knockout. Has delta integrated PDC activated in blue light & ScILV2 activated in the dark. |
| YEZ133 | YEZ117 + EZ_L316, Lost Plasmid | OptoINVRT3 in a PDC1, PDC5, PDC6, GAL80 a Knockout. Has delta integrated PDC activated in blue light & ScILV2 activated in the dark. |
| YEZ139 | CEN.PK2-1C HIS3::P$_{TEF1}$_VP16-EL222 T$_{CYC1}$_P$_{C120}$_GFP_T$_{ADH1}$ | All Integrated OptoEXP driving GFP |
| YEZ140 | CEN.PK2-1C HIS3$_{cg}$ | Control for CEN.PK2-1C |
| YEZ144 | YEZ115 + EZ_L235, Lost Plasmid | OptoINVRT1 in a PDC1, PDC5, PDC6, GAL80 a Knockout. Has delta integrated PDC activated in blue light & LDH activated in the dark. |
| YEZ145 | YEZ116 + EZ_L235, Lost Plasmid | OptoINVRT2 in a PDC1, PDC5, PDC6, GAL80 a Knockout. Has delta integrated PDC activated in blue light & LDH activated in the dark. |
| YEZ146 | YEZ117 + EZ_L235, Lost Plasmid | OptoINVRT3 in a PDC1, PDC5, PDC6, GAL80 a Knockout. Has delta integrated PDC activated in blue light & LDH activated in the dark. |
| YEZ149 | YEZ116 + EZ_L316, Lost Plasmid | OptoINVRT2 in a PDC1, PDC5, PDC6, GAL80 a Knockout. Has delta integrated PDC activated in blue light & ScILV2 activated in the dark. |
| YEZ156 | YEZ149 + EZ_L310 | OptoINVRT2 in a PDC1, PDC5, PDC6, GAL80 a Knockout. Has delta integrated PDC activated in blue light & ScILV2 activated in the dark. All mitochondrially-linked pathway enzymes to isobutanol in plasmid. |
| YEZ158 | YEZ115 bat1Δ1 + EZ_L316, Lost Plasmid | OptoINVRT1 in a PDC1, PDC5, PDC6, GAL80 a Knockout. Has delta integrated PDC activated in blue light & ScILV2 activated in the dark. BAT1 Knockout. |

SUPPLEMENTARY TABLE 2-continued

Yeast Strains Utilized

| Strain Name | Genotype | Description |
| --- | --- | --- |
| YEZ159 | YEZ131 + EZ_L310 | OptoINVRT1 in a PDC1, PDC5, PDC6, GAL80 a Knockout. Has delta integrated PDC activated in blue light & ScILV2 activated in the dark. BAT1 Knockout. Also has all mitochondrially-linked pathway enzymes to isobutanol in a plasmid. |
| YEZ167 | YEZ158 + EZ_L310 | OptoINVRT1 in a PDC1, PDC5, PDC6, GAL80 a Knockout. Has delta integrated PDC activated in blue light & ScILV2 activated in the dark. BAT1 Knockout. All mitochondrially-linked pathway enzymes to isobutanol in plasmid. |
| YEZ169 | YEZ158 + pRSII416 | Control for YEZ167 - same genetics except without the mitochondrial-isobutanol pathway enzymes, but with an empty plasmid. |
| YEZ186 | CEN.PK2-1C HIS3::$P_{TEF1}$_GFP_$T_{ACT1}$ | Integration TEF control for CEN.PK2-1C |
| HPY6 | YEZ133 + EZ_L310 | OptoINVRT3 in a PDC1, PDC5, PDC6, GAL80 a Knockout. Has delta integrated PDC activated in blue light & ScILV2 activated in the dark. All mitochondrially-linked pathway enzymes to isobutanol in plasmid. |
| pYZ335 | BY4741 bat1Δ1 + pJA192 | Control for constitutive Isobutanol production without control of ethanol production. |

SUPPLEMENTARY TABLE 3

Example OptoINVRT Circuit Components

| Circuit (INVRT) | VP16-EL222 | Gal80 | Gal4 | GFP (Reporter) |
| --- | --- | --- | --- | --- |
| 1 | Under TEF1 Promoter | Under OptoEXP Promoter, 2 Copies | Under ADH1 Promoter | Under GAL1 Promoter |
| 2 | Under TEF1 Promoter | Under OptoEXP Promoter, 2 Copies | Under PGK1 Promoter | Under GAL1 Promoter |
| 3 | Under TEF1 Promoter | Under OptoEXP Promoter, 2 Copies | Under PGK1 Promoter, and fused to a Photosensitive degron | Under GAL1 Promoter |

SUPPLEMENTARY TABLE 4

Performance of Example Circuits

| OptoINVRT Circuit | Strain | Leakiness (Dark/Light) | % of $P_{TEF1}$ |
| --- | --- | --- | --- |
| 1 | YEZ44 (CEN.PK2-1C gal4 gal80) | 45.75 | 73.08 |
| 2 | YEZ44 | 10.70 | 84.79 |
| 3 | YEZ44 | 70.41 | 20.82 |
| 1 | Y202 (BY4741 pdc1Δ1 pdc5Δ1 pdc6Δ1 gal80Δ1 + $P_{TEF1}$_PDC1_$T_{ACT1}$ in 2μ URA3 plasmid) | 7.44 | 91.99 |
| 2 | Y202 | 3.08 | 108.62 |
| 3 | Y202 | 27.42 | 56.43 |

Figure 24:
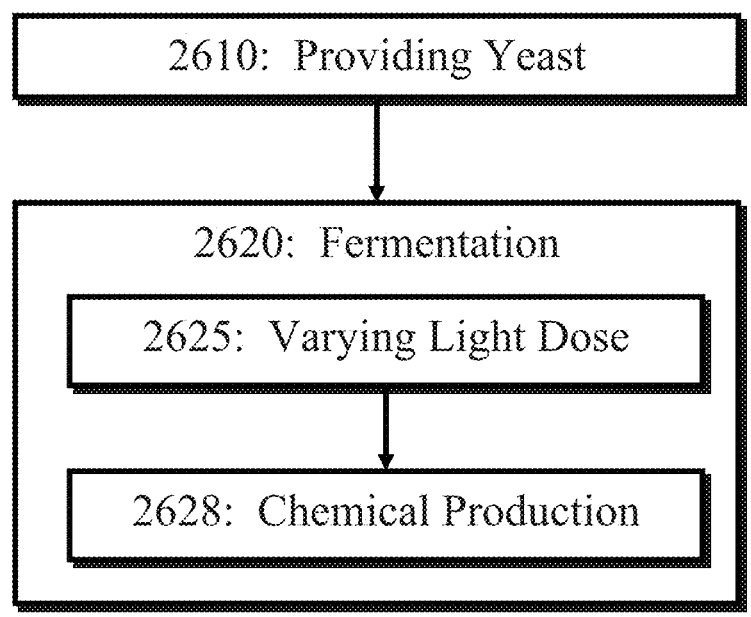
FIGS. 24 and 25 are flowcharts depicting the method for controlling the expression of genes in yeast.

A general method for controlling the expression of genes in, for example, yeast, for the purpose of producing a desired, valuable end product is shown in FIG. 24. The first step involves providing a modified strain of yeast (2610).

In general, the yeast cell should comprise a plurality of genes capable of being controlled bi-directionally with light, where one gene is turned from off to on when exposed to light (and the reverse when the light is turned off), and another gene that turned from on to off when exposed to light (and the reverse when the light is turned off).

The yeast cells are then fermented, typically using an appropriately selected growth medium, if needed. The fermentation phase (2620) is characterized by varying the light dose (2625) the yeast is exposed to in some fashion such as by varying the peak wavelength, intensity, duty cycle, or distance from one or more light sources. Doing so enables the overproduction of a chemical (2628) beyond what is produced by a wild-type strain.

Figure 25:
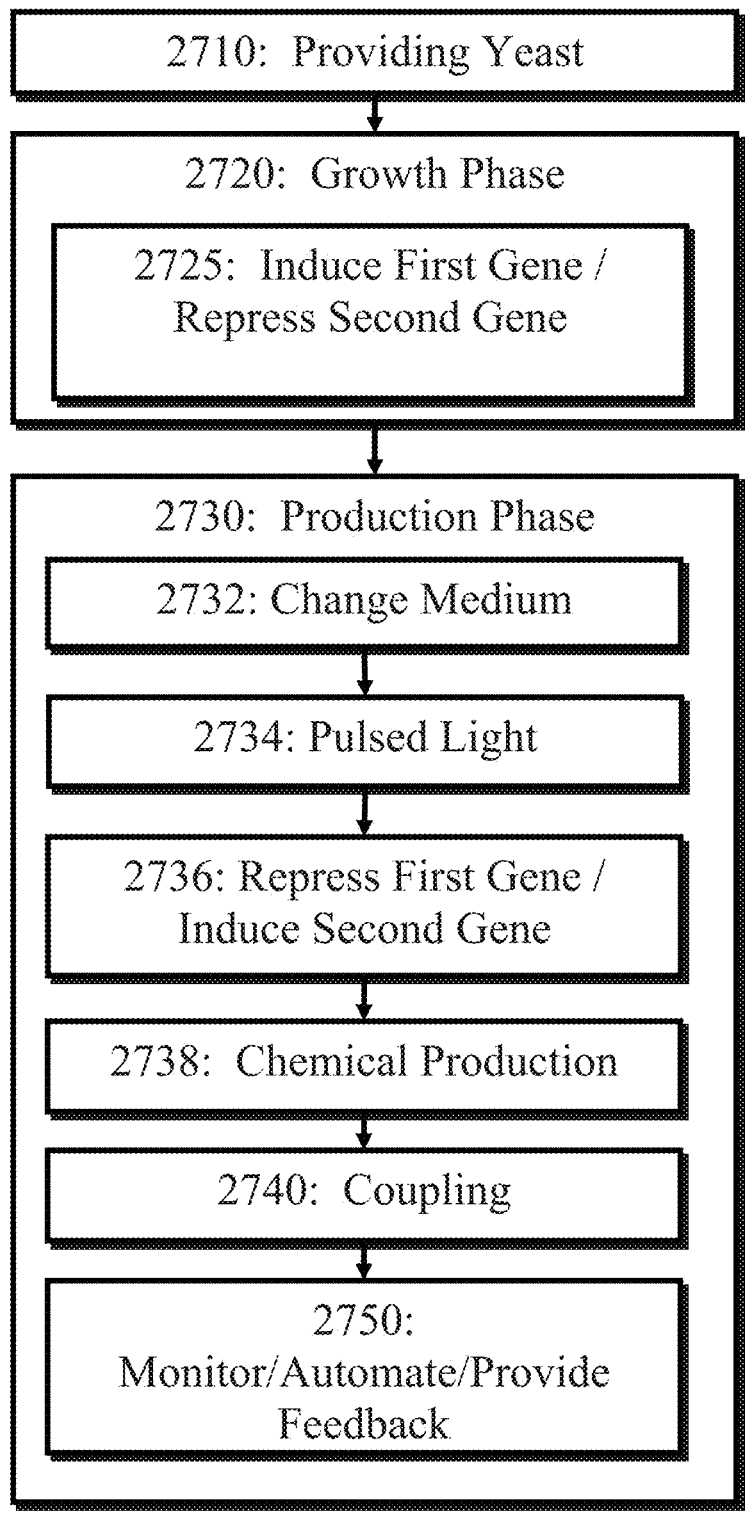

FIG. 25 illustrates an example of a more complex methodology. The first step still requires providing a modified strain of yeast (2710). However, the fermentation phase (2620) is now divided into at least two separate phases, a growth phase (2720) and a production phase (2730).

The growth phase (2720) is characterized by controlling the light so as to induce essential genes for growth and repress genes for toxic products (2725). For example, in some embodiments, PDC1 and GAL80 are induced, where at least PDC1 is an essential gene for growth of the yeast, while Gal4p-activated genes are repressed in the light due to Gal80p repression of Gal4p.

In some embodiments, the growth medium is changed or refreshed when switching from the growth phase to the production phase (2732). The production phase (2730) generally requires controlling the light to essentially invert the growth phase: repress the essential genes for growth, and induce the genes for toxic products (2736). This is generally done by stopping irradiation or altering the peak wavelength to fall outside the wavelength range that induces the essential genes. For example, a blue light could be turned off, or a yellow or infrared light could be turned on instead.

In the above example, PDC1 and GAL80 may be repressed, while Gal4p-activated genes are induced during the production phase. This results in the overproduction of at least one desired chemical (2738), such as lactic acid (for example, if the Gal4p-activated gene is LDH), or isobutanol, 2-methyl-1-butanol, or isopentanol (3-methyl-1-butanol) (for example, if the Gal4p-activated gene is ILV2), producing more of the desired chemical than would be produced by a wild-type strain. Among other benefits, this inversion step (2736) prevents the essential genes for growth from competing for resources with the genes for desired (and potentially toxic) products. Some embodiments utilize periodic light pulses during fermentation (2734) for repressing and inducing genes. These periodic light pulses are shown in FIG. 25 as occurring in the production phase, although it can be used at any time during fermentation.

In preferred embodiments, the method also includes coupling (2740) the production of the chemical with a biosensor or protein cascade system that produces a visual result in response to the presence of the chemical. These visual results can be measured or detected for a variety of reasons, including but not limited to monitoring the production of the chemical or providing feedback to a controller or automating at least some portion of the fermentation process. In preferred embodiments, the controller automates or adjusts the light schedule or various other process parameters of the fermentation phase, including temperature or mixing speeds, in order to further increase the overproduction of a desired chemical.

Combining optogenetics and metabolic engineering is not without its challenges. The high cell densities usually associated with microbial fermentations might be predicted to severely limit light penetration or prevent homogeneous responses to light. However, the disclosed approach resolves both concerns. Saturating light inputs need only be applied during an initial "growth phase" when culture density is not restrictive. During the "production phase", the inverted response of OptoINVRT circuits induces the metabolic pathways of interest in the dark, which is homogeneous and unimpeded by cell density. Furthermore, using sequences such as VP-EL222, which are highly light sensitive, with rapid light activation (<10 seconds) and relatively long half-life of its activated state (29 seconds), avoids the need for constant cell illumination, and provides effective light stimulation in relatively high cell densities, without high phototoxic light intensities. This is demonstrated by the light-dependent growth of YEZ167-4 in a 2-liter reactor, which reaches the same optical density as a wild-type strain control, and in the efficacy of light pulses during fed-batch fermentation to produce isobutanol and 2-methyl-1-butanol.

This system displays a complex relationship between the optical density at which cells are shifted from light to dark ($\rho$), the incubation time in the dark ($\theta$), and the eventual titers of desired products such as lactate or isobutanol. This complexity likely arises from a number of sources. As yeast cells grow in the light they accumulate Gal80p and Pdc1p. During incubation time $\theta$, protein turnover and mitotic dilution decrease the levels of Gal80p and Pdc1p, leading to Gal4p inducing expression of genes from $P_{GAL1}$ (inducing LDH or ILV2), and reduced competition from ethanol production, respectively. The lower the cell density $\rho$, the more mitotic cycles are available to dilute Gal80p and Pdc1p during time $\theta$. However, this decreases the total biomass (because low Pdc1p levels slow growth rate), which in turn decreases product output. The design features of each OptoINVRT circuit add to this complexity, providing versatility for different metabolic engineering applications.

The disclosed system of optogenetic regulation of engineered metabolic pathways provides a solution to the challenge of ethanol competition in branched-chain alcohol production. The disclosed light-controlled metabolic valve offers an efficient alternative to genetically deleting essential pathway genes (such as the combined deletion of PDC1, PDC5, and PDC6) that compete with pathway of interest. After optimization, this system can produce at least 10.5 g/L of total branched-chain alcohols (8.2 g/L of isobutanol, and 2.3 g/L of 2-methyl-1-butanol).

Thus, specific compositions, systems, and methods of light-activated gene transcription of metabolic enzymes for metabolic pathway tuning and induction of promoter cascades have been disclosed. It should be apparent, however, to those skilled in the art that many more modifications besides those already described are possible without departing from the inventive concepts herein. The inventive subject matter, therefore, is not to be restricted except in the spirit of the disclosure. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

In addition, the references listed herein and in the appended material are also part of the application and are incorporated by reference in their entirety as if fully set forth herein.

What is claimed is:

1. A yeast cell comprising:

a plurality of genes capable of being controlled bi-directionally with at least one wavelength of light, the plurality of genes capable of expressing enzymes for a metabolic pathway and expressing enzymes for an engineered biosynthetic pathway for overproduction of a chemical of interest, the plurality of genes comprising:

a first gene configured such that the first gene is expressed when exposed to the at least one wavelength of light, and the first gene is not expressed when not exposed or when exposed to a different wavelength of light; and a second gene configured such that the second gene is not expressed when exposed to the at least one wavelength of light, and the second gene is expressed when not exposed or when exposed to a different wavelength of light, wherein the plurality of genes includes:

a first sequence comprising a nucleotide sequence that encodes a light-activated transcription factor that binds to a first promoter and initiates transcription under certain wavelengths;

a second sequence comprising a second promoter which can be activated by the light-activated transcription factor encoded by the first sequence, the second sequence further comprising a nucleotide sequence that encodes for a first metabolic enzyme;

a third sequence comprising a third promoter which can be activated by the light-activated transcription factor encoded by the first sequence, and further comprising a nucleotide sequence that encodes a repressor; and a fourth sequence comprising a fourth promoter which can be repressed by the repressor encoded by the third sequence, and further comprising a nucleotide sequence that encodes a second metabolic enzyme, wherein the yeast cell is an *S. cerevisiae* cell, and wherein the first promoter is a constitutive promoter, the light-activated transcription factor is derived from a light-oxygen voltage (LOV) sensing domain, CRY2, CM, or the phytochrome B (PhyB) and PIF3 binding domain, the first metabolic enzyme is required for cell growth, the repressor is GAL80, and the fourth promoter is a galactose-inducible promoter via GAL4, and the second metabolic enzyme is an enzyme that drives the desired metabolic pathway to completion.

2. The yeast cell according to claim 1, wherein the light-activated transcription factor is EL222 and the fourth promoter is a GAL1 promoter, and the second metabolic enzyme is LDH or ILV2.

3. The yeast cell according to claim 1, wherein the first metabolic enzyme required for cell growth is PDC1.

4. The yeast cell according to claim 1, wherein the second metabolic enzyme is LDH, ILV2, ILV3, ILV5, or KDC.

* * * * *

SEQUENCE LISTING

<160> NUMBER OF SEQ ID NOS: 6

<210> SEQ ID NO 1
<211> LENGTH: 32
<212> TYPE: PRT
<213> ORGANISM: Artificial Sequence
<220> FEATURE:
<223> OTHER INFORMATION: Minimal Promoter Sequence

<400> SEQUENCE: 1

Thr Ala Gly Ala Gly Gly Gly Thr Ala Thr Ala Thr Ala Ala Thr Gly
1               5                   10                  15

Gly Ala Ala Gly Cys Thr Cys Gly Ala Cys Thr Thr Cys Cys Ala Gly
                20                  25                  30

<210> SEQ ID NO 2
<211> LENGTH: 178
<212> TYPE: PRT
<213> ORGANISM: Artificial Sequence
<220> FEATURE:
<223> OTHER INFORMATION: CLN2 PEST tag

<400> SEQUENCE: 2

Ala Ser Asn Leu Asn Ile Ser Arg Lys Leu Thr Ile Ser Thr Pro Ser
1               5                   10                  15

Cys Ser Phe Glu Asn Ser Asn Ser Thr Ser Ile Pro Ser Pro Ala Ser
                20                  25                  30

Ser Ser Gln Ser His Thr Pro Met Arg Asn Met Ser Ser Leu Ser Asp
            35                  40                  45

Asn Ser Val Phe Ser Arg Asn Met Glu Gln Ser Ser Pro Ile Thr Pro
50                  55                  60

Ser Met Tyr Gln Phe Gly Gln Gln Gln Ser Asn Ser Ile Cys Gly Ser
65                  70                  75                  80

Thr Val Ser Val Asn Ser Leu Val Asn Thr Asn Lys Gln Arg Ile
                85                  90                  95

Tyr Glu Gln Ile Thr Gly Pro Asn Ser Asn Ala Thr Asn Asp Tyr
                100                 105                 110

Ile Asp Leu Leu Asn Leu Asn Glu Ser Asn Lys Glu Asn Gln Asn Pro
            115                 120                 125

Ala Thr Ala His Tyr Leu Asn Gly Gly Pro Pro Lys Thr Ser Phe Ile
        130                 135                 140

Asn His Gly Met Phe Pro Ser Pro Thr Gly Thr Ile Asn Ser Gly Lys
145                 150                 155                 160

Ser Ser Ser Ala Ser Ser Leu Ile Ser Phe Gly Met Gly Asn Thr Gln
                165                 170                 175

Val Ile

<210> SEQ ID NO 3
<211> LENGTH: 16
<212> TYPE: PRT
<213> ORGANISM: Artificial Sequence
<220> FEATURE:
<223> OTHER INFORMATION: CL1 mutant tag
<300> PUBLICATION INFORMATION:
<301> AUTHORS: Cilon, Chomsky, Kulka
<302> TITLE: Degradation Signals Recognized by the Ubc6p-Ubc7p
      Ubiquitin-Conjugating Enzyme Pair
<303> JOURNAL: Molecular and Cellular Biology
<304> VOLUME: 20
<306> PAGES: 7214-7219
<307> DATE: 2000-10

```
<300> PUBLICATION INFORMATION:
<301> AUTHORS: Gilon, Tamar
<302> TITLE: Degradation Signals Recognized by the Ubc6p-Ubc7p
      Ubiquitin-Conjugating Enzyme Pair
<303> JOURNAL: Molecular and Cellular Biology
<304> VOLUME: 20
<306> PAGES: 7214-7219
<307> DATE: 2000-10

<400> SEQUENCE: 3

Ala Cys Lys Asn Trp Phe Ser Ser Leu Ser Ala Phe Val Ile Ala Leu
1               5                   10                  15

<210> SEQ ID NO 4
<211> LENGTH: 43
<212> TYPE: PRT
<213> ORGANISM: Artificial Sequence
<220> FEATURE:
<223> OTHER INFORMATION: ODC mutant tag
<300> PUBLICATION INFORMATION:
<301> AUTHORS: Takeuchi, Chen, Hoyt, Coffino
<302> TITLE: Structural elements of the ubiquitin-independent proteasome
      degron of ornithine decarboxylase
<303> JOURNAL: Biochemical Journal
<304> VOLUME: 410
<305> ISSUE: 2
<306> PAGES: 401-407
<307> DATE: 2008-03-01
<300> PUBLICATION INFORMATION:
<301> AUTHORS: Takeuchi, Junko
<302> TITLE: Structural elements of the ubiquitin-independent proteasome
      degron of ornithine decarboxylase
<303> JOURNAL: Biochemical Journal
<304> VOLUME: 410
<305> ISSUE: 2
<306> PAGES: 401-407
<307> DATE: 2008-03-01

<400> SEQUENCE: 4

Phe Pro Pro Glu Val Glu Glu Gln Asp Asp Gly Thr Leu Pro Met Ser
1               5                   10                  15

Cys Ala Gln Glu Ser Gly Met Asp Arg His Pro Ala Ser Cys Pro Glu
            20                  25                  30

Arg Ala Ala Cys Ala Ser Ala Arg Ile Asn Val
        35                  40

<210> SEQ ID NO 5
<211> LENGTH: 499
<212> TYPE: PRT
<213> ORGANISM: Artificial Sequence
<220> FEATURE:
<223> OTHER INFORMATION: PGAL1 mutant

<400> SEQUENCE: 5

Ala Gly Cys Thr Gly Gly Ala Gly Cys Thr Cys Ala Cys Cys Gly Gly
1               5                   10                  15

Thr Ala Thr Ala Cys Cys Cys Gly Gly Gly Cys Gly Gly Ala Thr Thr
            20                  25                  30

Ala Gly Ala Ala Gly Cys Cys Gly Cys Cys Gly Ala Gly Cys Gly Gly
        35                  40                  45

Gly Thr Gly Ala Cys Ala Gly Cys Cys Thr Cys Cys Gly Ala Ala Ala
    50                  55                  60

Gly Gly Ala Ala Gly Ala Cys Thr Cys Thr Cys Cys Thr Cys Cys Gly
65                  70                  75                  80

Thr Gly Cys Gly Thr Cys Cys Thr Cys Gly Thr Cys Thr Thr Cys Ala
                85                  90                  95
```

```
Cys Cys Gly Gly Thr Cys Gly Cys Gly Thr Thr Cys Cys Thr Gly Ala
            100                 105                 110

Ala Ala Cys Gly Cys Ala Gly Ala Thr Gly Thr Gly Cys Cys Thr Cys
        115                 120                 125

Gly Cys Gly Cys Cys Gly Cys Ala Cys Thr Gly Cys Thr Cys Cys Gly
    130                 135                 140

Ala Ala Cys Ala Ala Thr Ala Ala Ala Gly Ala Thr Thr Cys Thr Ala
145                 150                 155                 160

Cys Ala Ala Thr Ala Cys Thr Ala Gly Cys Thr Thr Thr Thr Ala Thr
                165                 170                 175

Gly Gly Thr Thr Ala Thr Gly Ala Ala Gly Ala Gly Gly Ala Ala Ala
            180                 185                 190

Ala Ala Thr Thr Gly Gly Cys Ala Gly Thr Ala Ala Cys Cys Thr Gly
        195                 200                 205

Gly Thr Thr Gly Gly Thr Ala Ala Ala Ala Cys Cys Thr Thr Cys Ala
    210                 215                 220

Ala Ala Thr Gly Ala Ala Cys Gly Ala Ala Thr Cys Ala Ala Ala Thr
225                 230                 235                 240

Thr Ala Ala Cys Ala Ala Cys Cys Ala Thr Ala Gly Gly Ala Thr Gly
                245                 250                 255

Ala Thr Ala Ala Thr Gly Cys Gly Ala Thr Thr Ala Gly Thr Thr Thr
            260                 265                 270

Thr Thr Thr Ala Gly Cys Cys Thr Thr Ala Thr Thr Thr Thr Ala Gly
        275                 280                 285

Thr Ala Gly Thr Ala Ala Thr Thr Ala Ala Thr Cys Ala Gly Cys Gly
    290                 295                 300

Ala Ala Gly Cys Gly Ala Thr Gly Ala Thr Thr Thr Thr Thr Gly Ala
305                 310                 315                 320

Thr Cys Thr Ala Thr Thr Ala Ala Cys Ala Gly Ala Thr Ala Thr Ala
                325                 330                 335

Thr Ala Ala Ala Thr Gly Cys Ala Ala Ala Ala Ala Cys Thr Gly Cys
            340                 345                 350

Ala Thr Ala Ala Cys Cys Ala Cys Thr Thr Thr Ala Ala Cys Thr Ala
        355                 360                 365

Ala Thr Ala Cys Thr Thr Thr Cys Ala Ala Cys Ala Thr Thr Thr Thr
    370                 375                 380

Cys Gly Gly Thr Thr Thr Gly Thr Ala Thr Thr Ala Cys Thr Thr Cys
385                 390                 395                 400

Thr Thr Ala Thr Thr Cys Ala Ala Ala Thr Gly Thr Ala Ala Thr Ala
                405                 410                 415

Ala Ala Ala Gly Thr Ala Thr Cys Ala Ala Cys Ala Ala Ala Ala Ala
            420                 425                 430

Ala Thr Thr Gly Thr Thr Ala Ala Thr Ala Thr Ala Cys Cys Thr Cys
        435                 440                 445

Thr Ala Thr Ala Cys Thr Thr Thr Ala Ala Cys Gly Thr Cys Ala Ala
    450                 455                 460

Gly Gly Ala Gly Ala Ala Ala Ala Ala Ala Cys Thr Ala Thr Ala Gly
465                 470                 475                 480

Cys Gly Gly Cys Cys Gly Cys Thr Ala Ala Ala Ala Thr Cys Ala Thr
                485                 490                 495

Gly Gly Cys
```

<210> SEQ ID NO 6
<211> LENGTH: 699
<212> TYPE: PRT
<213> ORGANISM: Artificial Sequence
<220> FEATURE:
<223> OTHER INFORMATION: PGAL1 mutant

<400> SEQUENCE: 6

```
Ala Gly Cys Thr Cys Ala Cys Cys Gly Gly Thr Ala Thr Ala Cys Cys
1               5                   10                  15

Cys Gly Gly Gly Cys Gly Gly Ala Thr Ala Gly Ala Ala Gly Cys
                20                  25                  30

Cys Gly Cys Cys Gly Ala Gly Cys Gly Gly Thr Gly Ala Cys Ala
            35                  40                  45

Gly Cys Cys Cys Thr Cys Cys Gly Ala Ala Gly Gly Ala Ala Gly Ala
50                  55                  60

Cys Thr Cys Thr Cys Cys Thr Cys Cys Gly Thr Gly Cys Gly Thr Cys
65                  70                  75                  80

Cys Thr Cys Gly Thr Cys Thr Thr Cys Ala Cys Cys Gly Gly Thr Cys
                85                  90                  95

Gly Cys Gly Thr Thr Cys Cys Thr Gly Ala Ala Ala Cys Gly Cys Ala
                100                 105                 110

Gly Ala Thr Gly Thr Gly Cys Cys Thr Cys Gly Cys Gly Cys Cys Gly
            115                 120                 125

Cys Ala Cys Thr Gly Cys Thr Cys Cys Gly Ala Ala Cys Ala Ala Thr
130                 135                 140

Ala Ala Ala Gly Ala Thr Thr Cys Thr Ala Cys Ala Ala Thr Ala Cys
145                 150                 155                 160

Thr Ala Gly Cys Thr Thr Thr Thr Ala Thr Gly Gly Thr Thr Ala Thr
                165                 170                 175

Gly Ala Ala Gly Ala Gly Gly Ala Ala Ala Ala Thr Thr Gly Gly
            180                 185                 190

Ala Thr Gly Ala Thr Thr Thr Thr Gly Ala Thr Cys Thr Ala Thr
        195                     200                 205

Thr Ala Ala Cys Ala Gly Ala Thr Ala Thr Ala Ala Ala Thr
210                 215                 220

Gly Cys Ala Ala Ala Ala Cys Gly Gly Ala Thr Thr Ala Gly Ala
225                 230                 235                 240

Ala Gly Cys Cys Gly Cys Cys Gly Ala Gly Cys Gly Gly Gly Thr Gly
                245                 250                 255

Ala Cys Ala Gly Cys Cys Cys Thr Cys Cys Gly Ala Ala Gly Gly Ala
            260                 265                 270

Ala Gly Ala Cys Thr Cys Thr Cys Cys Thr Cys Cys Gly Thr Gly Cys
        275                 280                 285

Gly Thr Cys Cys Thr Cys Gly Thr Cys Thr Thr Cys Ala Cys Cys Gly
    290                 295                 300

Gly Thr Cys Gly Cys Gly Thr Thr Cys Cys Thr Gly Ala Ala Ala Cys
305                 310                 315                 320

Gly Cys Ala Gly Ala Thr Gly Thr Gly Cys Cys Thr Cys Gly Cys Gly
                325                 330                 335

Cys Cys Gly Cys Ala Cys Thr Gly Cys Thr Cys Cys Gly Ala Ala Cys
            340                 345                 350

Ala Ala Thr Ala Ala Ala Gly Ala Thr Thr Cys Thr Ala Cys Ala Ala
        355                 360                 365
```

```
Thr Ala Cys Thr Ala Gly Cys Thr Thr Thr Ala Thr Gly Gly Thr
    370             375             380

Thr Ala Thr Gly Ala Ala Gly Ala Gly Gly Ala Ala Ala Ala Thr
385             390             395             400

Thr Gly Gly Cys Ala Gly Thr Ala Ala Cys Cys Thr Gly Thr Thr
            405             410             415

Gly Gly Thr Ala Ala Ala Ala Cys Cys Thr Thr Cys Ala Ala Thr
            420             425             430

Gly Ala Ala Cys Gly Ala Ala Thr Cys Ala Ala Ala Thr Ala Ala
            435             440             445

Cys Ala Ala Cys Cys Ala Thr Ala Gly Gly Ala Thr Gly Ala Thr Ala
    450             455             460

Ala Thr Gly Cys Gly Ala Thr Thr Ala Gly Thr Thr Thr Thr Thr
465             470             475             480

Ala Gly Cys Cys Thr Thr Ala Thr Thr Thr Ala Gly Thr Ala Gly
            485             490             495

Thr Ala Ala Thr Thr Ala Ala Thr Cys Ala Gly Cys Gly Ala Ala Gly
        500             505             510

Cys Gly Ala Thr Gly Ala Thr Thr Thr Thr Gly Ala Thr Cys Thr
    515             520             525

Ala Thr Thr Ala Ala Cys Ala Gly Ala Thr Ala Thr Ala Thr Ala Ala
    530             535             540

Ala Thr Gly Cys Ala Ala Ala Ala Cys Thr Gly Cys Ala Thr Ala
545             550             555             560

Ala Cys Cys Ala Cys Thr Thr Thr Ala Ala Cys Thr Ala Ala Thr Ala
            565             570             575

Cys Thr Thr Thr Cys Ala Ala Cys Ala Thr Thr Thr Cys Gly Gly
            580             585             590

Thr Thr Thr Gly Thr Ala Thr Thr Ala Cys Thr Thr Cys Thr Thr Ala
        595             600             605

Thr Thr Cys Ala Ala Ala Thr Gly Thr Ala Ala Thr Ala Ala Ala
    610             615             620

Gly Thr Ala Thr Cys Ala Ala Cys Ala Ala Ala Ala Ala Thr Thr
625             630             635             640

Gly Thr Thr Ala Ala Thr Ala Thr Ala Cys Cys Thr Cys Thr Ala Thr
            645             650             655

Ala Cys Thr Thr Thr Ala Ala Cys Gly Thr Cys Ala Ala Gly Gly Ala
            660             665             670

Gly Ala Ala Ala Ala Ala Ala Cys Thr Ala Thr Ala Gly Cys Gly Gly
            675             680             685

Cys Cys Gly Cys Thr Ala Ala Ala Ala Thr Cys
    690             695
```